(12) United States Patent
Davis et al.

(10) Patent No.: US 12,312,418 B2
(45) Date of Patent: May 27, 2025

(54) ORTHOGONAL MUTATIONS FOR HETERODIMERIZATION

(71) Applicant: Invenra Inc., Madison, WI (US)

(72) Inventors: Jonathan Harry Davis, Madison, WI (US); Nicholas M. Marshall, Middleton, WI (US)

(73) Assignee: Invenra Inc., Madison, WI (US)

( * ) Notice: Subject to any disclaimer, the term of this patent is extended or adjusted under 35 U.S.C. 154(b) by 652 days.

(21) Appl. No.: 17/548,375

(22) Filed: Dec. 10, 2021

(65) Prior Publication Data

US 2022/0363782 A1 Nov. 17, 2022

Related U.S. Application Data

(60) Provisional application No. 63/123,915, filed on Dec. 10, 2020.

(51) Int. Cl.
*C07K 16/46* (2006.01)
*A61K 39/00* (2006.01)

(52) U.S. Cl.
CPC ........... *C07K 16/468* (2013.01); *A61K 39/00* (2013.01); *C07K 2317/31* (2013.01); *C07K 2317/35* (2013.01); *C07K 2317/50* (2013.01); *C07K 2317/526* (2013.01); *C07K 2317/56* (2013.01); *C07K 2317/569* (2013.01); *C07K 2317/60* (2013.01); *C07K 2317/64* (2013.01)

(58) Field of Classification Search
CPC .............. C07K 16/468; C07K 2317/31; C07K 2317/35; C07K 2317/50; C07K 2317/526; C07K 2317/56; C07K 2317/569; C07K 2317/60; C07K 2317/64; C07K 16/00; A61K 39/00

See application file for complete search history.

(56) References Cited

U.S. PATENT DOCUMENTS

| | | | |
|---|---|---|---|
| 2012/0149876 A1* | 6/2012 | Von Kreudenstein | C07K 16/00 530/387.3 |
| 2015/0307628 A1 | 10/2015 | Kim et al. | |
| 2018/0118811 A1* | 5/2018 | Glaser | A61P 35/02 |
| 2019/0169252 A1 | 6/2019 | Kim et al. | |
| 2019/0367628 A1* | 12/2019 | Abujoub | A61P 35/00 |
| 2020/0255522 A1* | 8/2020 | Brinkmann | C07K 16/461 |

FOREIGN PATENT DOCUMENTS

| | | | |
|---|---|---|---|
| CA | 2815266 A1 * | 5/2012 | ............. A61P 35/00 |
| WO | WO-2014138449 A1 * | 9/2014 | ............. A61P 35/00 |
| WO | WO-2016130516 A1 * | 8/2016 | ............. A61P 35/00 |
| WO | WO-2018148447 A1 * | 8/2018 | ............. A61P 35/00 |
| WO | WO 2019/204522 A1 | 10/2019 | |
| WO | WO 2020/216878 A1 | 10/2020 | |
| WO | WO 2021/168379 A1 | 8/2021 | |

OTHER PUBLICATIONS

Brinkman, U. et al. "The Making of Bispecific Antibodies." mAbs, vol. 9, No. 2, Jan. 10, 2017, pp. 182-212.
PCT International Search Report and Written Opinion, PCT Application No. PCT/US2021/062951, Apr. 4, 2022, 14 pages.

* cited by examiner

*Primary Examiner* — Chun W Dahle
*Assistant Examiner* — Grace H Lunde
(74) *Attorney, Agent, or Firm* — Fenwick & West LLP

(57) ABSTRACT

Heterodimerizing domains with orthogonal mutations that drive heterodimerization, in particular heterodimerizing antibody CH3 domains, heterodimeric polypeptides comprising such heterodimerizing domains, and antibody constructs comprising such heterodimeric polypeptides, are provided.

1 Claim, 21 Drawing Sheets

Specification includes a Sequence Listing.

"X" = D,E,F,H,M,N,Q,R,S,T,W, or Y
or
"X" = A,D,E,F,G,H,I,L,M,N,P,Q,R,S,T,V,W, or Y

"Z" = A,D,E,H,K,L,N,Q,T,W, or Y
or
"Z" = A,D,E,F,G,H,I,K,L,M,N,P,Q,R,T,V,W, or Y

BC-1

BC-6

SEQUENCE LISTING

<160> NUMBER OF SEQ ID NOS: 28

<210> SEQ ID NO 1
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Ile Lys Gly Gln Pro Arg Glu Pro Gln Val Cys Thr Leu Pro Pro
1               5                   10                  15

Ser Arg Asp Glu Leu Thr Lys Asn Gln Val Ser Leu Thr Cys Leu Val
            20                  25                  30

Arg Gly Phe Tyr Pro Ser Asp Ile Ala Val Glu Trp Glu Ser Asn Gly
        35                  40                  45

Gln Pro Glu Asn Asn Tyr Lys Thr Thr Pro Pro Val Leu Asp Ser Asp
    50                  55                  60

Gly Ser Phe Phe Leu Tyr Ser Lys Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu Ser Pro Gly Lys Asp Lys
            100                 105                 110

Thr His Thr Cys Pro Pro Cys Pro Ala Pro Glu Leu Leu Gly Gly Pro
        115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
    210                 215                 220

Thr Ile Ser Lys Ala Lys Gly Gln Pro Arg Glu Pro Gln Val Tyr Thr
225                 230                 235                 240

Leu Pro Pro Ser Arg Asp Glu Leu Thr Lys Asn Gln Val Ser Leu Trp
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys

```
<210> SEQ ID NO 2
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Val Ser Ser Ala Gln Pro Arg Glu Pro Gln Val Tyr Thr Leu Pro Pro
1               5                   10                  15

Cys Arg Asp Trp Leu Thr Lys Asn Gln Val Ser Leu Thr Cys Leu Val
            20                  25                  30

Lys Gly Phe Tyr Pro Ser Asp Ile Ala Val Glu Trp Glu Ser Asn Gly
        35                  40                  45

Gln Pro Glu Asn Asn Tyr Lys Thr Thr Pro Pro Val Leu Asp Ser Asp
    50                  55                  60

Gly Ser Phe Phe Leu Tyr Ser Lys Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110

<210> SEQ ID NO 3
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Ile Lys Arg Thr Val Ala Ala Pro Ser Val Phe Ile Phe Pro Pro
1               5                   10                  15

Ser Asp Glu Gln Leu Lys Ser Gly Thr Ala Ser Val Val Cys Leu Leu
            20                  25                  30

Asn Asn Phe Tyr Pro Arg Glu Ala Lys Val Gln Trp Lys Val Asp Asn
        35                  40                  45

Ala Leu Gln Ser Gly Asn Ser Gln Glu Ser Val Thr Glu Gln Asp Ser
    50                  55                  60

Lys Asp Ser Thr Tyr Ser Leu Ser Ser Thr Leu Thr Leu Ser Lys Ala
65                  70                  75                  80

Asp Tyr Glu Lys His Lys Val Tyr Ala Cys Glu Val Thr His Gln Gly
                85                  90                  95

Leu Ser Ser Pro Val Thr Lys Ser Phe Asn Arg Gly Glu Cys Asp Lys
            100                 105                 110

Thr His Thr Cys Pro Pro Cys Pro Ala Pro Glu Leu Leu Gly Gly Pro
        115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
```

```
                195                 200                 205
Tyr Lys Cys Lys Val Ser Asn Lys Ala Leu Pro Ala Pro Ile Glu Lys
            210                 215                 220

Thr Ile Ser Lys Ala Lys Gly Gln Pro Arg Glu Pro Gln Val Tyr Thr
225                 230                 235                 240

Leu Pro Pro Ser Arg Glu Glu Met Thr Lys Asn Gln Val Ser Leu Ser
            245                 250                 255

Cys Ala Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
            275                 280                 285

Asp Ser Asp Gly Ser Phe Phe Leu Val Ser Lys Leu Thr Val Asp Lys
            290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
            325                 330                 335

Lys

<210> SEQ ID NO 4
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Val Ser Ser Ala Ser Thr Lys Gly Pro Ser Val Phe Pro Leu Ala Pro
1               5                   10                  15

Ser Ser Lys Ser Thr Ser Gly Gly Thr Ala Ala Leu Gly Cys Leu Val
            20                  25                  30

Lys Asp Tyr Phe Pro Glu Pro Val Thr Val Ser Trp Asn Ser Gly Ala
        35                  40                  45

Leu Thr Ser Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Gln Thr Tyr Ile Cys Asn Val Asn His Lys Pro Ser Asn Thr Lys
                85                  90                  95

Val Asp Lys Lys Val Glu Pro Lys Ser Cys
            100                 105

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Gln Pro Arg Glu Pro Gln Val Cys Thr Leu Pro Pro Ser Arg Asp
1               5                   10                  15

Glu Leu Thr Lys Asn Gln Val Ser Leu Thr Cys Leu Val Arg Gly Phe
            20                  25                  30

Tyr Pro Ser Asp Ile Ala Val Glu Trp Glu Ser Asn Gly Gln Pro Glu
        35                  40                  45
```

```
Asn Asn Tyr Lys Thr Thr Pro Pro Val Leu Asp Ser Asp Gly Ser Phe
             50                   55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 6
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
                 20                  25                  30

Val Val Asp Val Ser His Glu Asp Pro Glu Val Lys Phe Asn Trp Tyr
             35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Gln Pro Arg Glu Pro Gln Val Tyr Thr Leu Pro Pro Ser Arg Asp
  1               5                  10                  15

Glu Leu Thr Lys Asn Gln Val Ser Leu Trp Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 8
```

<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Gln Pro Arg Glu Pro Gln Val Tyr Thr Leu Pro Pro Cys Arg Asp
1               5                   10                  15

Trp Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 10
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Gln Pro Arg Glu Pro Gln Val Tyr Thr Leu Pro Pro Ser Arg Glu
 1               5                   10                  15

Glu Met Thr Lys Asn Gln Val Ser Leu Ser Cys Ala Val Lys Gly Phe
                20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                  55                  60

Phe Leu Val Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105

<210> SEQ ID NO 12
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ala Ser Thr Lys Gly Pro Ser Val Phe Pro Leu Ala Pro Ser Ser Lys
 1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys
            100

<210> SEQ ID NO 13
<211> LENGTH: 1011
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 13

```
gagatcaagg gccagccccg ggagcccag gtctgtaccc tgccgccgtc acgggacgaa      60
ctcactaaga accaagtgtc cctgacttgc ctggtcagag gattctatcc gagcgacatc    120
gccgtggagt gggagtccaa cggccagccc gagaacaact acaagacgac accccggtg    180 cttgacagcg acggttcctt cttttttgtac tcgaagttga ccgtcgataa gtcacgctgg   240
caacagggaa acgtgttcag ctgctccgtg atgcacgaag ccctgcacaa ccactacacc   300
cagaagtctc tgagcctctc cccgggaaag gacaagactc acacgtgccc gccgtgccca   360
gcacctgagc tgttgggagg tcctagcgtg ttcctgttcc cgccgaagcc caaggacacc   420
ctgatgattt cgaggactcc ggaagtgacc tgtgtggtgg tggatgtgtc ccatgaggac   480
cccgaagtca aattcaattg gtacgtggat ggagtgaag tgcacaatgc caagactaag   540
cccagagaag aacagtacaa ctcgacctac cgcgtggtgt ccgtgctgac tgtgttgcat   600
caggactggc tcaacggaaa agagtacaag tgcaaagtct ccaacaaggc cctcccggca   660
ccgatcgaga aaaccatctc gaaagccaag ggccagcccc gggagcctca ggtctacacc   720
ctgccaccat cgcgggatga actcaccaag aaccaagtgt cgctgtggtg tctcgtgaag   780
ggcttttacc cttccgacat tgccgtggag tgggaatcca acgggcagcc tgaaaacaac   840
tacaagacca ccccgcccgt gctcgactcg gatggaagct tcttcctgta ctctaagctg   900
accgtggaca agtccggtg gcagcaggga aacgtgttca gctgctcggt catgcacgaa   960
gccctgcata accactacac ccagaagtca ctgtccctga cccggggaa g            1011
```

<210> SEQ ID NO 14
<211> LENGTH: 330
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 14

```
gtgtccagcg cccagccccg ggagcccag gtctacaccc tgccgccgtg tcgggactgg      60
ctcactaaga accaagtgtc cctgacttgc ctggtcaagg gattctatcc gagcgacatc    120
gccgtggagt gggagtccaa cggccagccc gagaacaact acaagacgac accccggtg    180 cttgacagcg acggttcctt cttttttgtac tcgaagttga ccgtcgataa gtcacgctgg   240
caacagggaa acgtgttcag ctgctccgtg atgcacgaag ccctgcacaa ccactacacc   300
cagaagtctc tgagcctctc cccgggaaag                                     330
```

<210> SEQ ID NO 15
<211> LENGTH: 1011
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 15

```
gagattaaga gaaccgtcgc agcccctcc gtgttcatct tccctccctc ggatgagcag      60
ctgaagtccg gcaccgcgag cgtggtctgc ctgctcaaca acttctatcc gcgggaagcg    120
aaggtccagt ggaaggtcga caacgccctg cagtcgggaa actcccagga gtccgtgact    180
gagcaggatt caaaggacag cacctactcc ctgtcgtcta ccctcaccct gagcaaggcc    240
gactacgaga agcacaaggt ctacgcctgc gaagtcacgc accaaggcct tagctcccct    300
gtgaccaagt cattcaaccg ggggagtgc gacaagactc acgtgccc gccgtgccca       360 gcacctgagc tgttgggagg tcctagcgtg ttcctgttcc cgccgaagcc caaggacacc    420
ctgatgattt cgaggactcc ggaagtgacc tgtgtggtgg tggatgtgtc ccatgaggac    480
cccgaagtca aattcaattg gtacgtggat ggagtggaag tgcacaatgc caagactaag    540
cccagagaag aacagtacaa ctcgacctac cgcgtggtgt ccgtgctgac tgtgttgcat    600
caggactggc tcaacggaaa agagtacaag tgcaaagtct ccaacaaggc cctcccggca    660
ccgatcgaga aaaccatctc gaaagccaag ggccagcccc gggaacctca agtctacact    720
ctgccaccct cgcgggaaga aatgaccaag aaccaagtgt ccctgagctg tgccgtgaag    780
ggcttctacc cgtccgacat cgccgtggaa tgggaatcga acgggcagcc ggagaacaat    840
tacaagacca cccctcccgt gctggacagc gatggatcgt tcttcctggt gtccaagctc    900
actgtggaca gtcgcggtg gcagcaggga acgtgttta gctgctccgt gatgcacgag      960
gccctgcata accactacac ccagaagtcc ctgtccctct cacccgggaa g            1011
```

<210> SEQ ID NO 16
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
gtatcaagcg cctcaactaa gggcccctcg gtgttccctc tggccccgag ctccaagtcg     60
acctccggcg gtacagccgc tctgggttgc ctcgtgaagg actacttccc tgaaccagtg    120
accgtgtcct ggaactctgg ggcgctgacc agcggggtgc acactttccc ggcggtgctg    180
cagtcgtcgg gactgtactc cctgtcctcc gtcgtgacgg tgccctcctc ctcactgggc    240
acccagactt acatttgcaa cgtgaaccac aagccgagca acaccaaggt cgacaagaag    300
gtcgagccca agtcctgt                                                  318
```

<210> SEQ ID NO 17
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Glu Ile Lys Gly Gln Pro Arg Glu Pro Gln Val Cys Thr Leu Pro Pro
1               5                   10                  15

Ser Arg Asp Glu Leu Thr Lys Asn Gln Val Ser Leu Thr Cys Leu Val
            20                  25                  30

Lys Gly Phe Tyr Pro Ser Asp Ile Ala Val Glu Trp Glu Ser Asn Gly
        35                  40                  45

Gln Pro Glu Asn Asn Tyr Lys Thr Thr Pro Pro Val Leu Asp Ser Asp
    50                  55                  60
```

Gly Ser Phe Phe Leu Tyr Ser Lys Leu Thr Val Asp Lys Ser Arg Trp
65                  70                  75                  80

Gln Gln Gly Asn Val Phe Ser Cys Ser Val Met His Glu Ala Leu His
            85                  90                  95

Asn His Tyr Thr Gln Lys Ser Leu Ser Leu Ser Pro Gly Lys Asp Lys
                100                 105                 110

Thr His Thr Cys Pro Pro Cys Pro Ala Pro Glu Leu Leu Gly Gly Pro
            115                 120                 125

Ser Val Phe Leu Phe Pro Pro Lys Pro Lys Asp Thr Leu Met Ile Ser
    130                 135                 140

Arg Thr Pro Glu Val Thr Cys Val Val Val Asp Val Ser His Glu Asp
145                 150                 155                 160

Pro Glu Val Lys Phe Asn Trp Tyr Val Asp Gly Val Glu Val His Asn
                165                 170                 175

Ala Lys Thr Lys Pro Arg Glu Glu Gln Tyr Asn Ser Thr Tyr Arg Val
            180                 185                 190

Val Ser Val Leu Thr Val Leu His Gln Asp Trp Leu Asn Gly Lys Glu
        195                 200                 205

Tyr Lys Cys Lys Val Ser Asn Lys Ala Leu Pro Ala Pro Ile Glu Lys
    210                 215                 220

Thr Ile Ser Lys Ala Lys Gly Gln Pro Arg Glu Pro Gln Val Tyr Thr
225                 230                 235                 240

Leu Pro Pro Ser Arg Asp Glu Leu Thr Lys Asn Gln Val Ser Leu Trp
                245                 250                 255

Cys Leu Val Lys Gly Phe Tyr Pro Ser Asp Ile Ala Val Glu Trp Glu
            260                 265                 270

Ser Asn Gly Gln Pro Glu Asn Asn Tyr Lys Thr Thr Pro Pro Val Leu
        275                 280                 285

Asp Ser Asp Gly Ser Phe Phe Leu Tyr Ser Lys Leu Thr Val Asp Lys
    290                 295                 300

Ser Arg Trp Gln Gln Gly Asn Val Phe Ser Cys Ser Val Met His Glu
305                 310                 315                 320

Ala Leu His Asn His Tyr Thr Gln Lys Ser Leu Ser Leu Ser Pro Gly
                325                 330                 335

Lys

<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Val Ser Ser Ala Gln Pro Arg Glu Pro Gln Val Tyr Thr Leu Pro Pro
1               5                   10                  15

Cys Arg Asp Trp Leu Thr Lys Asn Gln Val Arg Leu Thr Cys Leu Val
            20                  25                  30

Lys Gly Phe Tyr Pro Ser Asp Ile Ala Val Glu Trp Glu Ser Asn Gly
        35                  40                  45

Gln Pro Glu Asn Asn Tyr Lys Thr Thr Pro Pro Val Leu Asp Ser Asp
    50                  55                  60

Gly Ser Phe Phe Leu Tyr Ser Lys Leu Thr Val Asp Lys Ser Arg Trp
65                  70                  75                  80

Gln Gln Gly Asn Val Phe Ser Cys Ser Val Met His Glu Ala Leu His
                85                  90                  95

Asn His Tyr Thr Gln Lys Ser Leu Ser Leu Ser Pro Gly Lys
            100                 105                 110

<210> SEQ ID NO 19
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gly Gln Pro Arg Glu Pro Gln Val Cys Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Gln Pro Arg Glu Pro Gln Val Tyr Thr Leu Pro Pro Cys Arg Asp
1               5                   10                  15

Trp Leu Thr Lys Asn Gln Val Arg Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 21

Asp Lys Thr His Thr
1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Gly Lys Cys
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Gly Lys Cys
1

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Gly Lys Gly Cys
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Gly Lys Gly Ser Cys
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Ile Lys Gly Gln Pro
1               5

<210> SEQ ID NO 27
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Ser Ser Ala Gln Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Pro Gly Lys Asp Lys
1               5
```

ORTHOGONAL MUTATIONS FOR HETERODIMERIZATION

1. CROSS-REFERENCE TO RELATION APPLICATIONS

This application claims the benefit of and priority to U.S. Provisional Application No. 63/123,915, filed Dec. 10, 2020, which is incorporated by reference in its entirety.

2. SEQUENCE LISTING

The instant application contains a Sequence Listing which has been submitted via EFS-Web and is hereby incorporated herein by reference in its entirety. Said ASCII copy, created on Apr. 21, 2022, is named 46256 US CRF sequencelisting.txt, and is 28,300 bytes in size.

3. BACKGROUND OF THE INVENTION

Proper assembly of protein heterodimers within a cell requires protein:protein interactions that favor heterodimerization over homodimerization of the constituent polypeptide chains. The need to drive specific association of distinct polypeptide chains increases as the number of polypeptides in the protein increases. For example, correct assembly of bivalent bispecific antibodies having two different heavy chains and two different light chains requires specific heterodimerization of the first light chain to the first heavy chain, second light chain to the second heavy chain, and the first heavy chain to the second heavy chain. Efficient assembly requires that the protein:protein interactions that drive association of the various heterodimers be different for each such heterodimeric pair.

A variety of orthogonal mutations have been developed that drive preferential heterodimerization of certain engineered antibody domains, including knob-in-hole (KIH) mutations, see e.g. U.S. Pat. Nos. 5,731,168; 5,807,706; and 5,821,333; charge pair mutations, see e.g. U.S. Pat. No. 9,358,286; disulfide-stabilized KIH mutations, see e.g. U.S. Pat. Nos. 7,951,917; 8,642,745 and 9,409,989; and others.

There is a need in the art for further approaches to driving specific heterodimerization and multimerization, to be used alone and in combination with known heterodimerization features.

4. SUMMARY OF THE INVENTION

We have engineered new orthogonal mutations that are capable of driving specific heterodimerization of multiple polypeptide chains, facilitating high fidelity association of polypeptides, particularly useful for multivalent, multispecific antibody constructs.

5. BRIEF DESCRIPTION OF THE SEVERAL VIEWS OF THE DRAWINGS

Figure 1A:
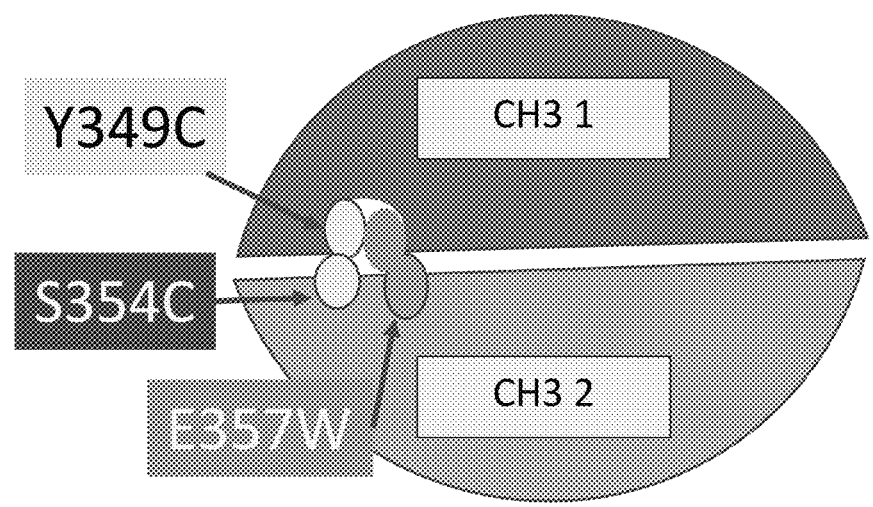
Figure 1B:
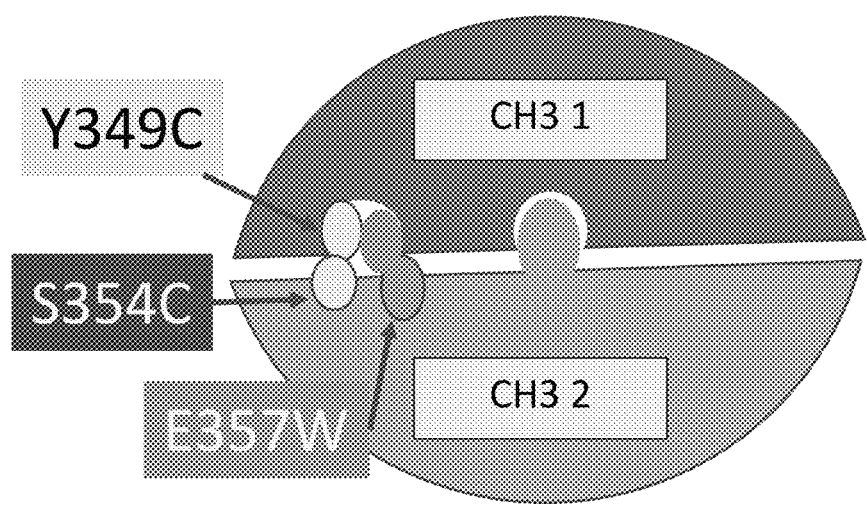
Figure 1C:
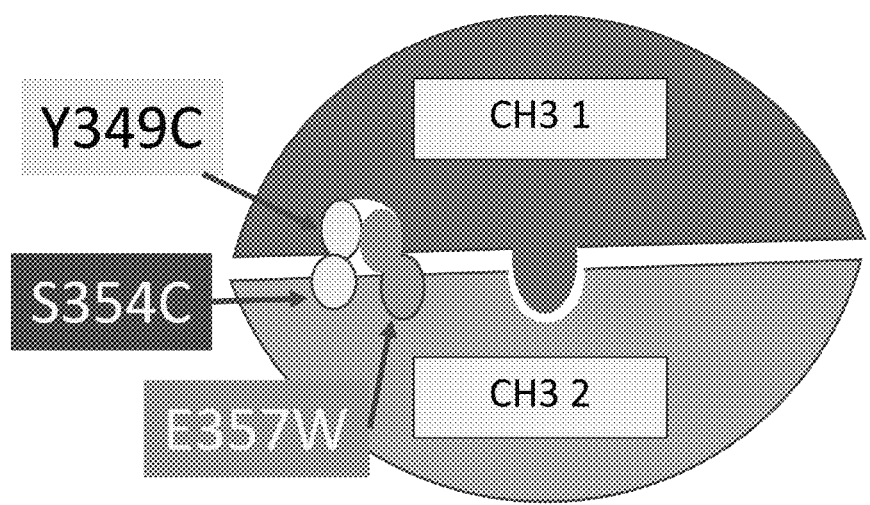
Figure 1D:
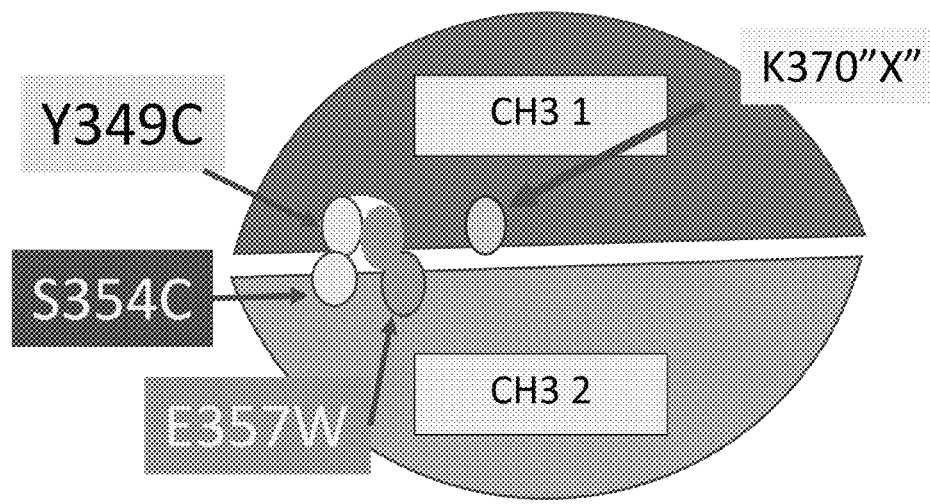
Figure 1E:
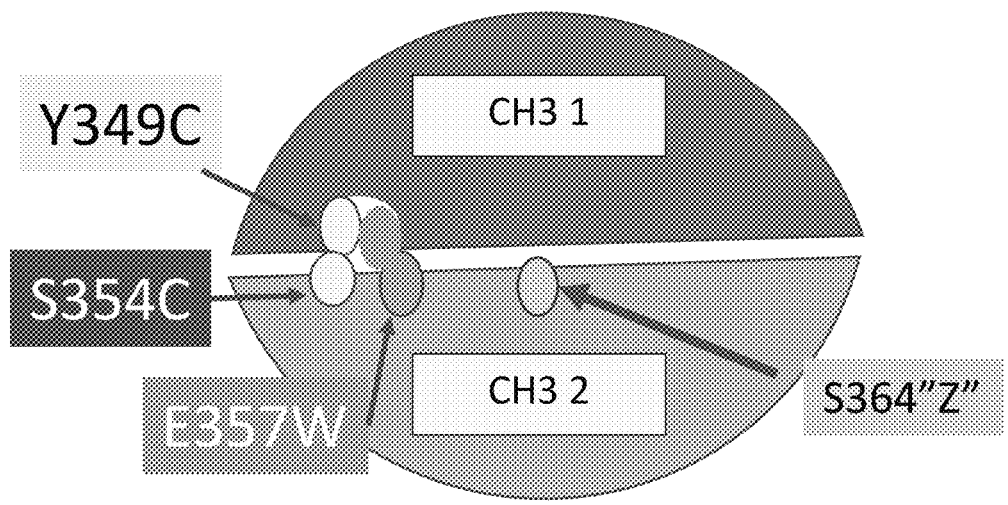

These and other features, aspects, and advantages of the present invention will become better understood with regard to the following description, and accompanying drawings, where:

FIGS. 1A-1E illustrate heterodimeric CH3 domains with exemplary orthogonal mutations of the present invention. FIG. 1A shows dimerized CH3 domains with no additional mutations. FIG. 1B shows dimerized CH3 domains with additional knob-in-hole mutations in which the knob is in the same domain as the E357W mutation. FIG. 1C shows dimerized CH3 domains with additional knob-in-hole mutations in which the knob is in the opposite domain from the E357W mutation. FIG. 1D shows further "cascade" mutations in the CH3 domain opposite the domain having an E357W mutation. FIG. 1E shows further "cascade" mutations in the CH3 domain that contains an E357W mutation.

Figure 2:
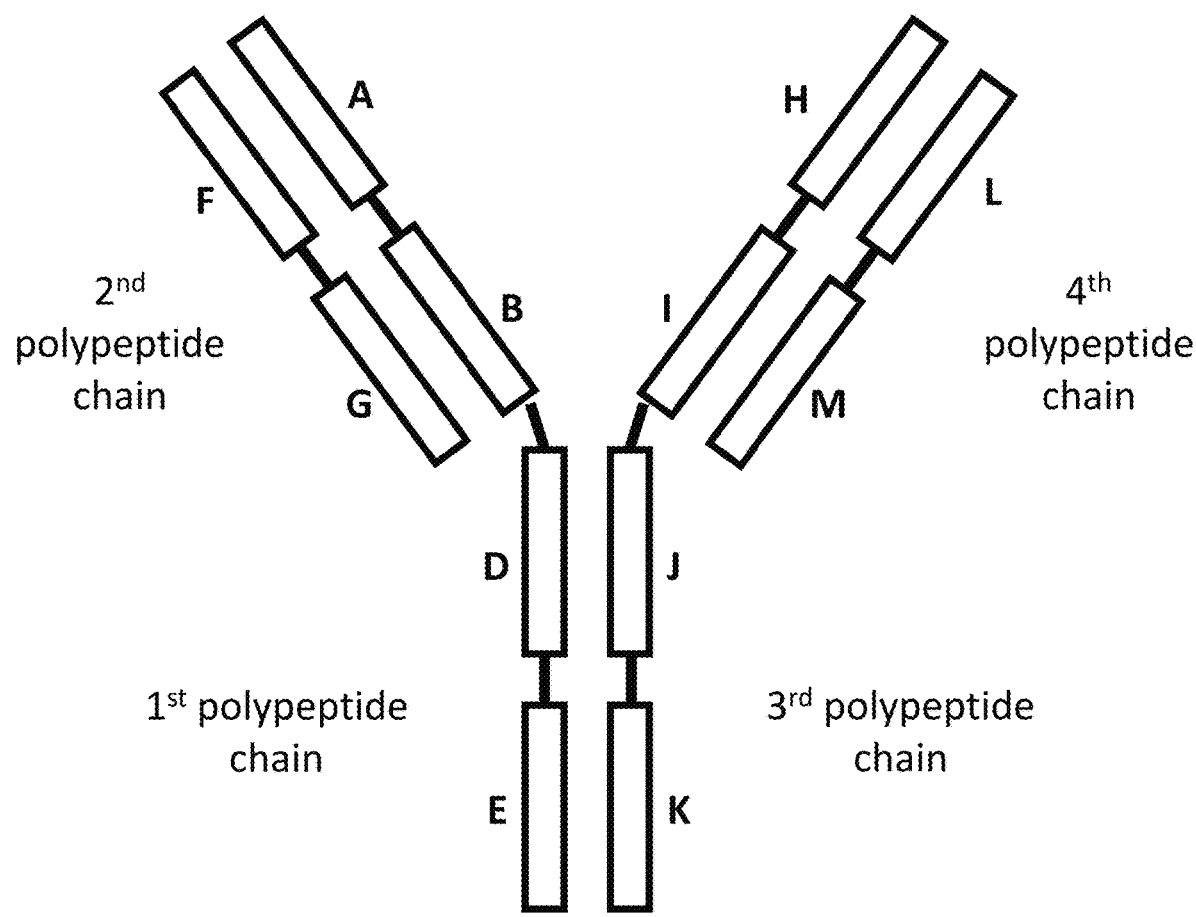

FIG. 2 presents a schematic architecture, with respective naming conventions, for various bivalent antibody constructs described herein.

Figure 3:
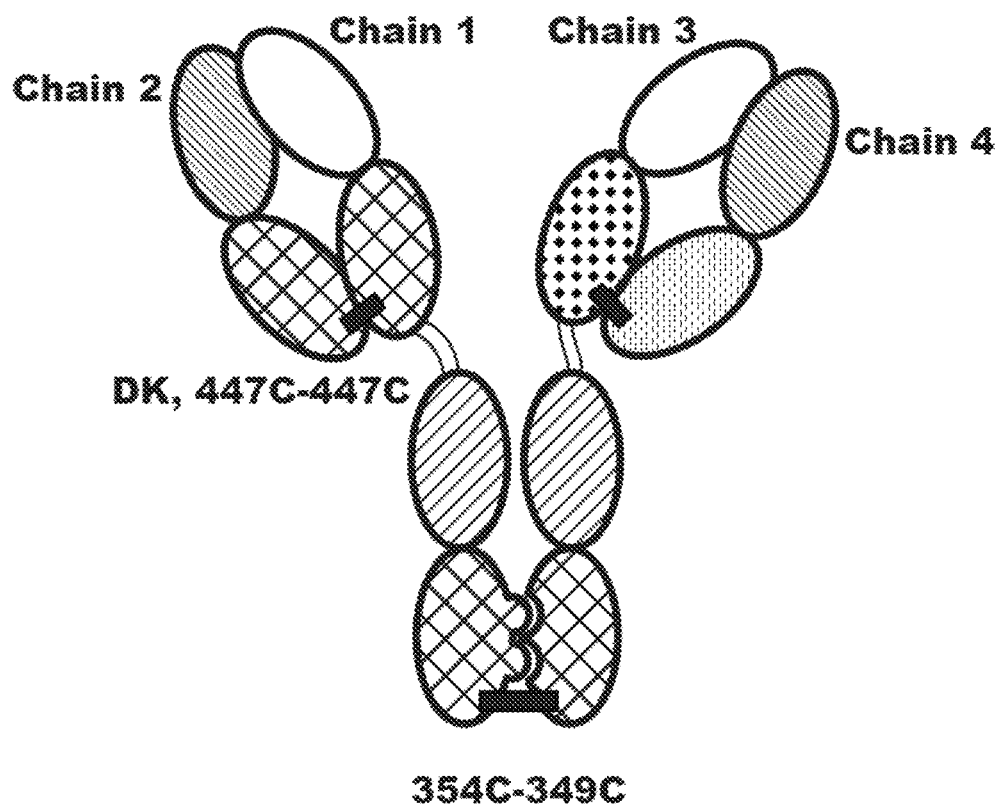
Figure 3:
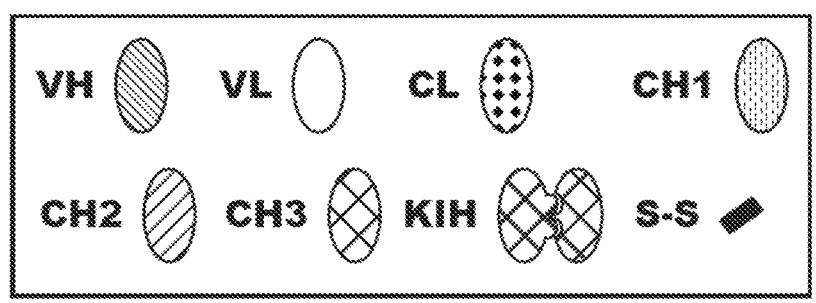

FIG. 3 presents a schematic showing the domain content of exemplary bivalent antibody construct "BC1". The orthogonal mutations described herein can be further engineered into the E:K paired domains.

Figure 4:
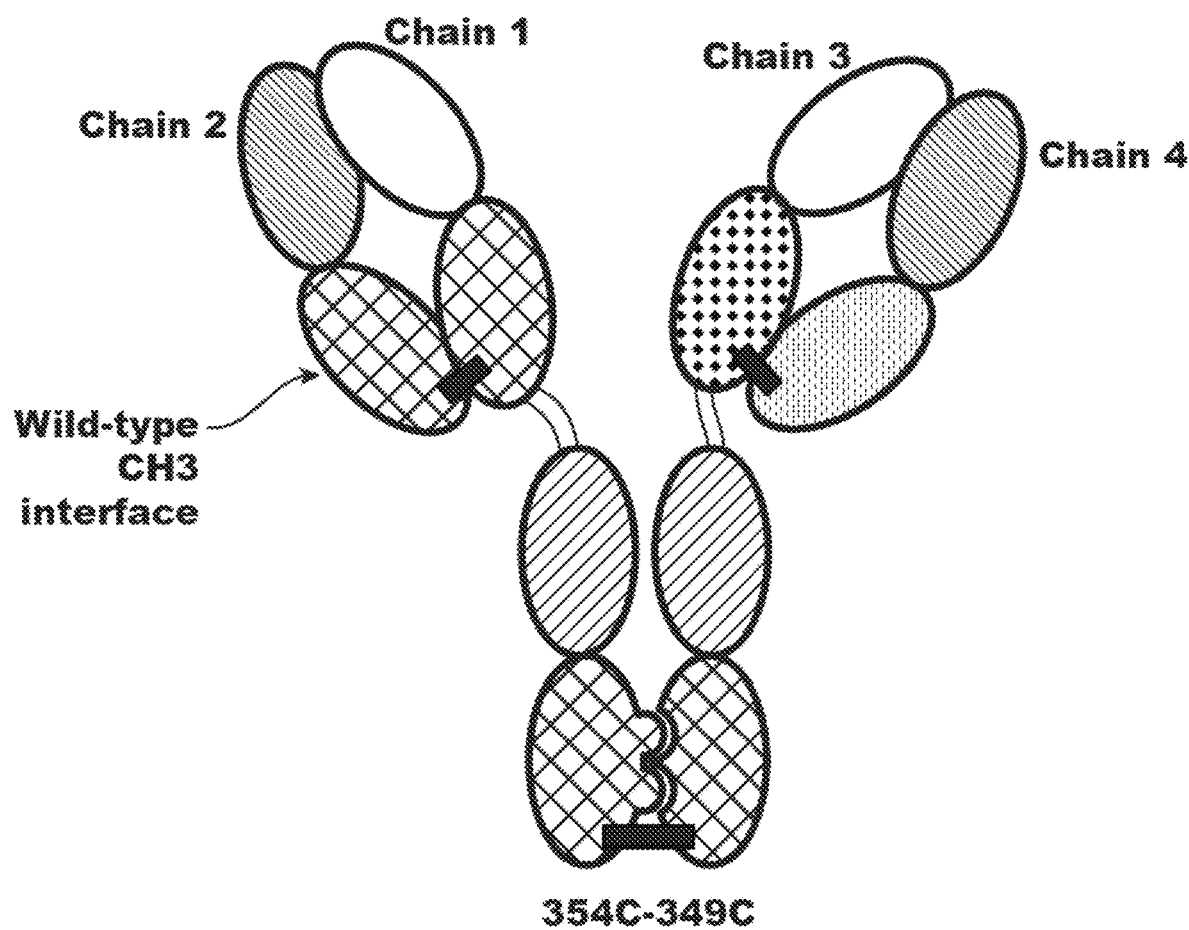
Figure 4:
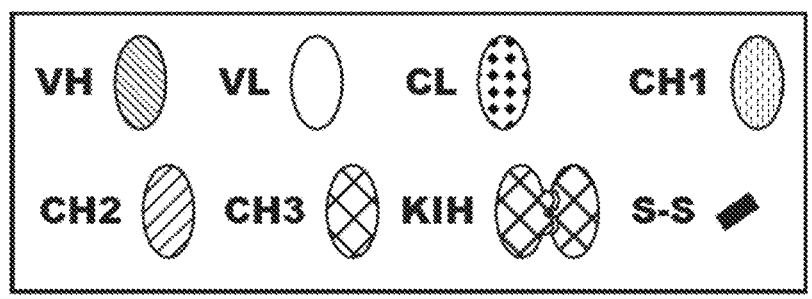

FIG. 4 presents a schematic showing the domain content of exemplary bivalent antibody construct "BC6". The orthogonal mutations described herein can be further engineered into the E:K paired domains.

Figure 5:
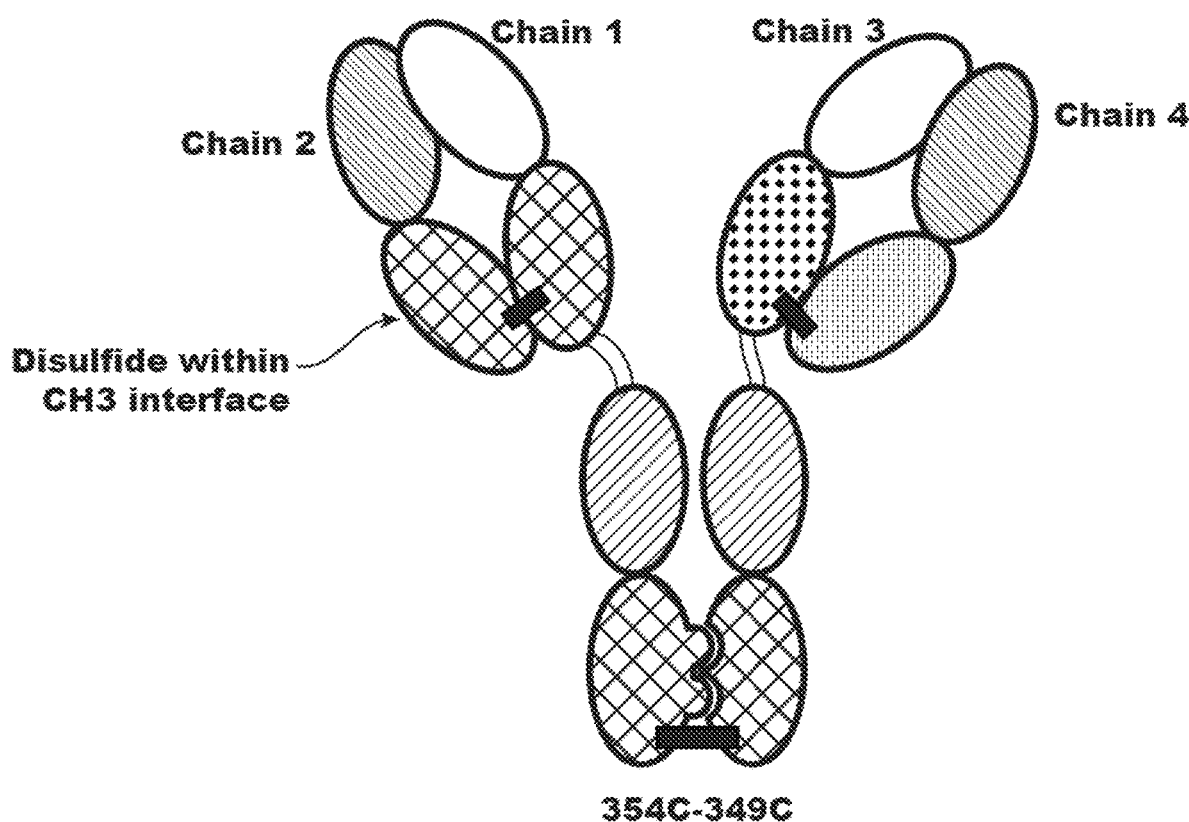
Figure 5:
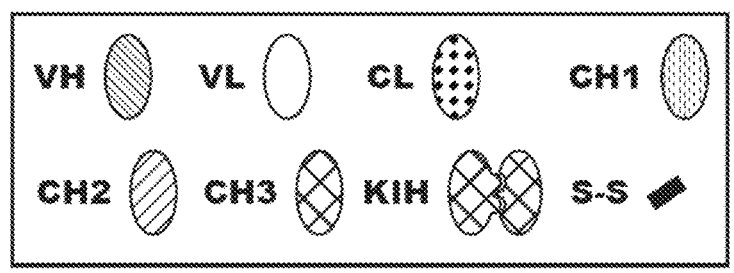

FIG. 5 presents a schematic showing the domain content of exemplary bivalent antibody construct "BC28". The orthogonal mutations described herein can be further engineered into the B:G paired domains or E:K paired domains.

Figure 6:
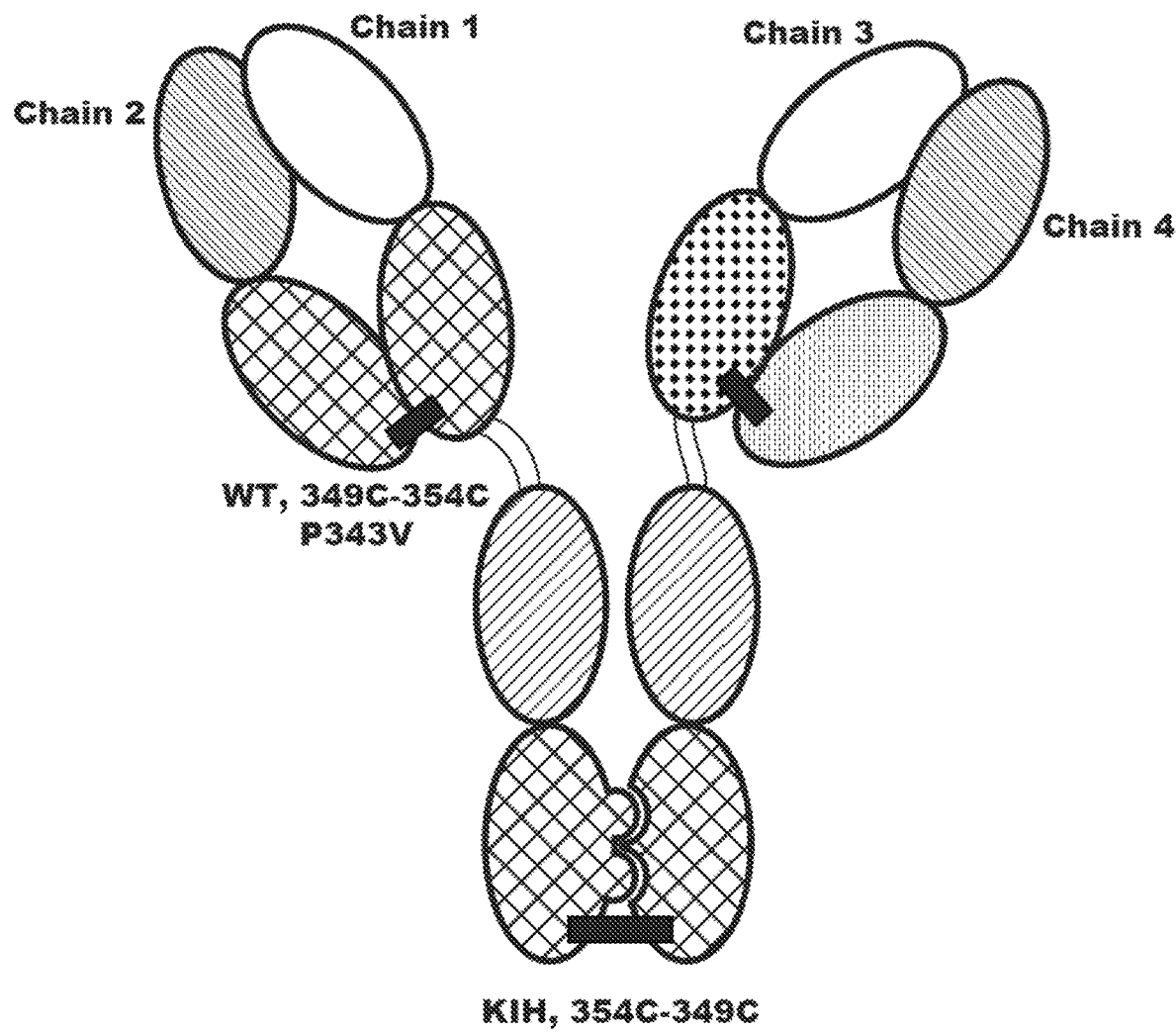

FIG. 6 presents a schematic showing the domain content of exemplary bivalent antibody construct "BC44". The orthogonal mutations described herein can be further engineered into the B:G paired domains or E:K paired domains.

Figure 7:
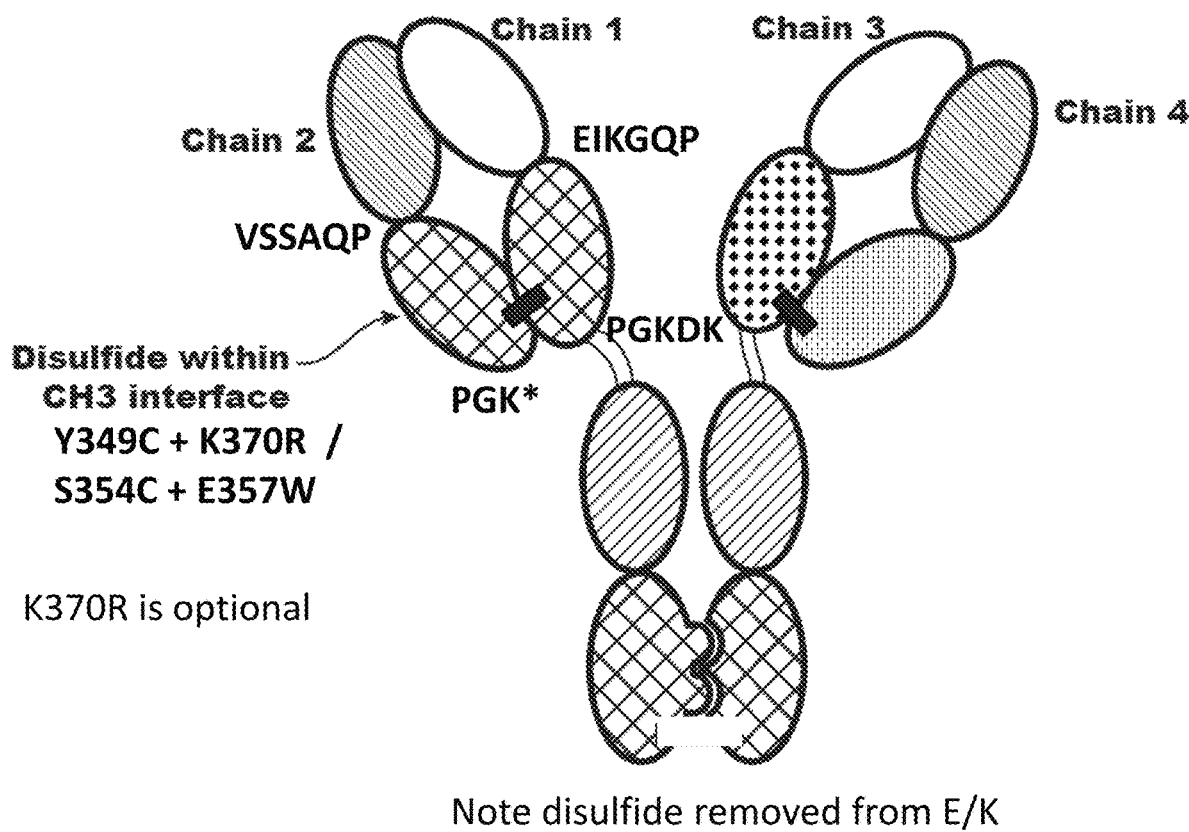
Figure 7:
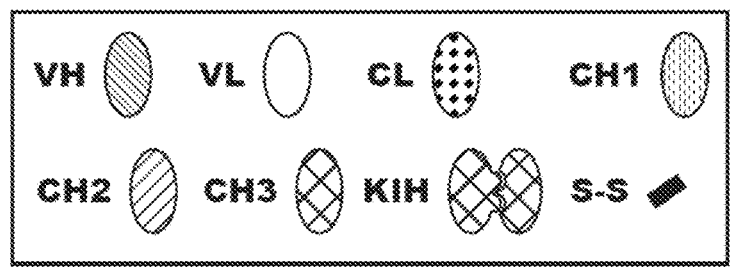

FIG. 7 presents a schematic showing the domain content of exemplary bivalent antibody construct "BC-96", which includes various orthogonal mutations described herein.

Figure 8A:
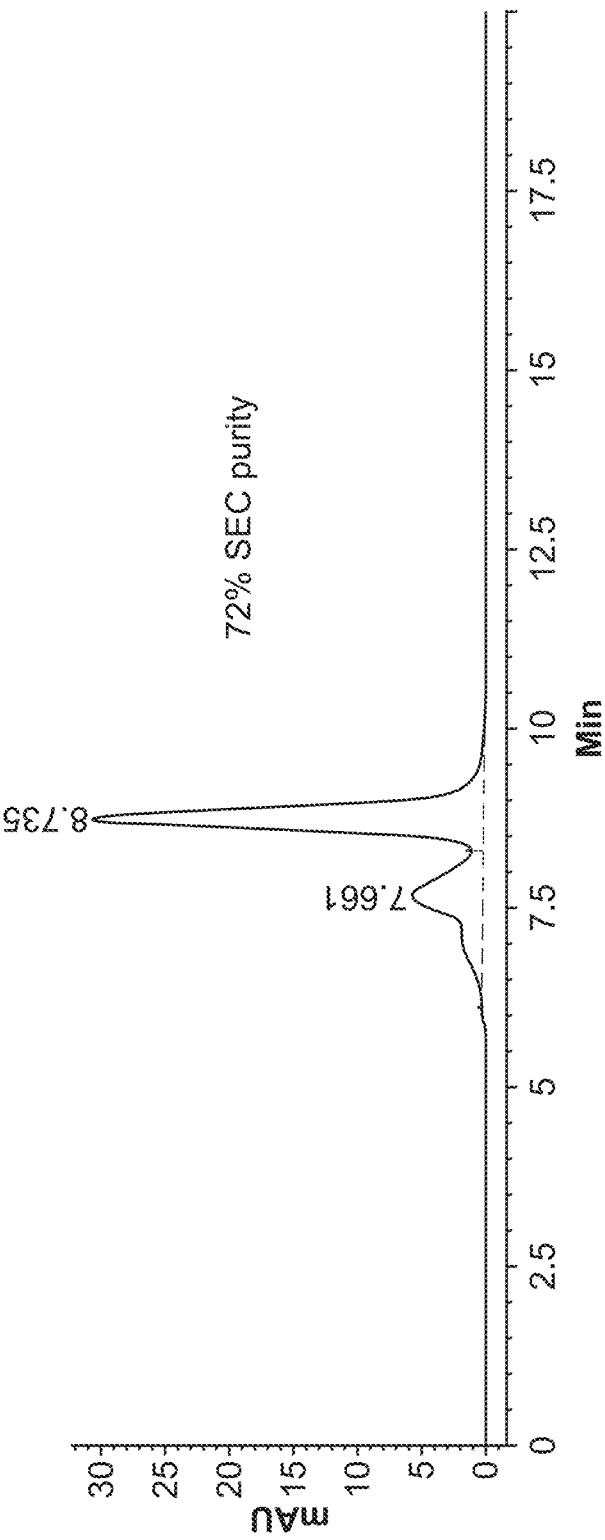
Figure 8B:
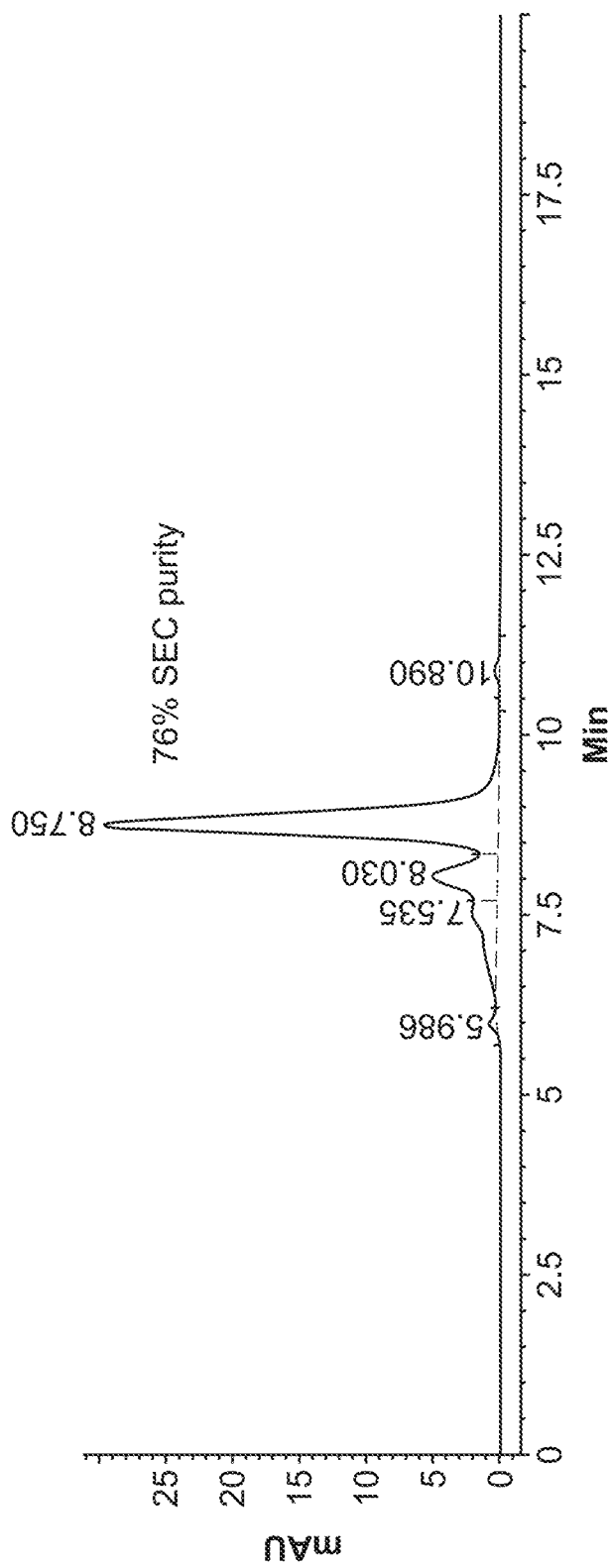
Figure 8C:
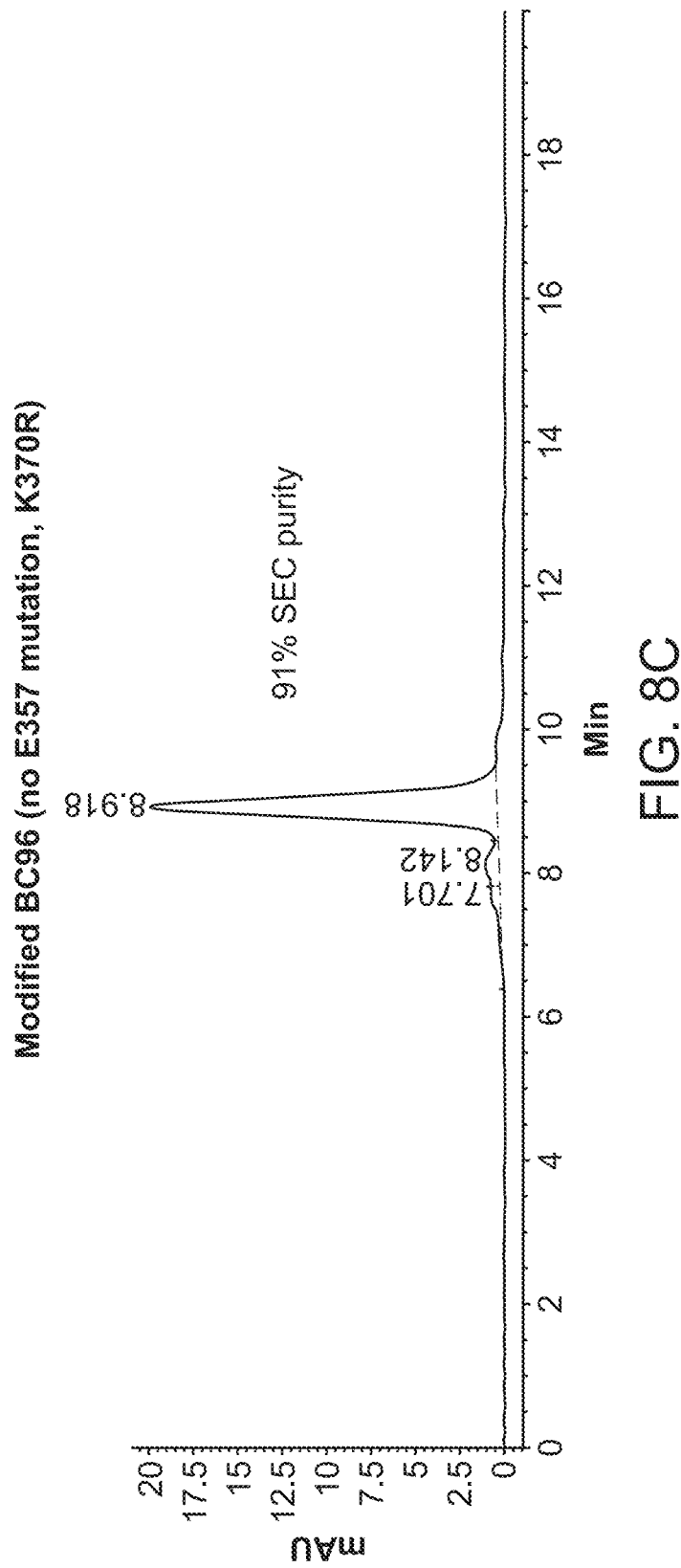
Figure 8D:
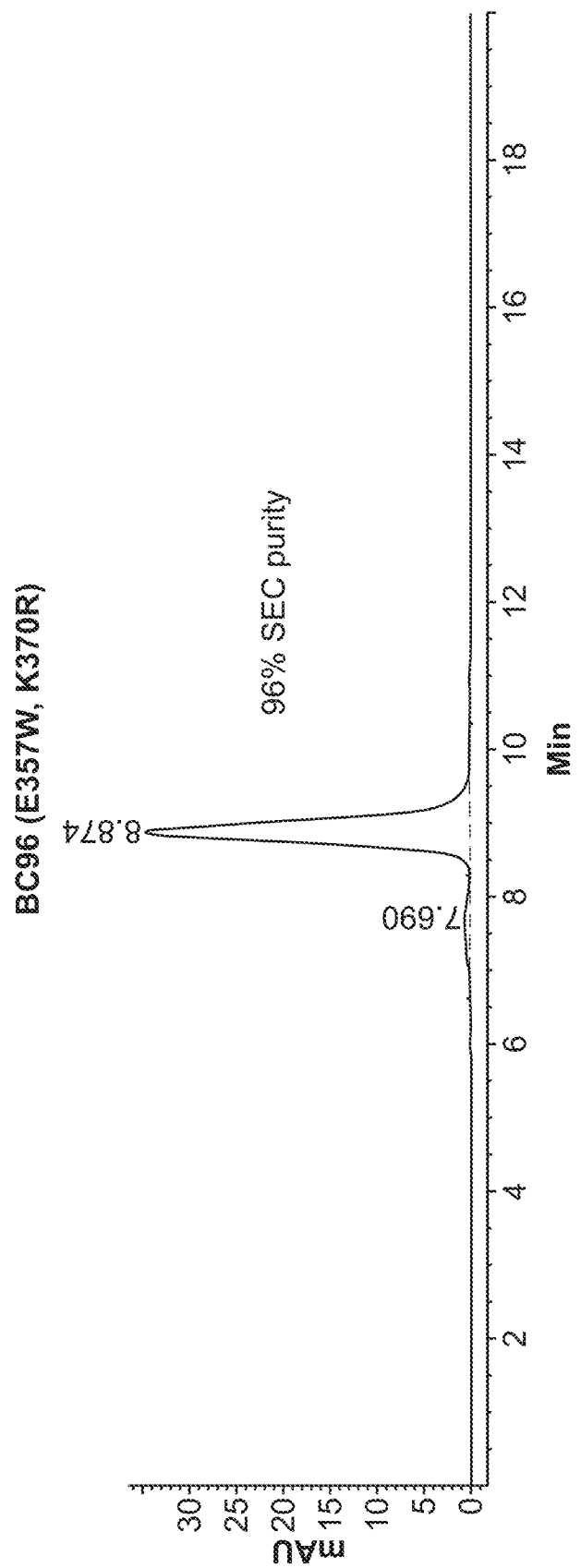

FIGS. 8A-8D show results of size exclusion chromatography (SEC) analysis following CH1 purification of BC96 and various alternatives. FIG. 8A shows results from a variant that differs from BC96 in that Domain B lacks a K370 mutation and Domain G lacks an E357 mutation. FIG. 8B shows results from a variant that differs from BC96 in that Domain B lacks a K370 mutation. FIG. 8C shows results from a variant that differs from BC96 in that Domain G lacks an E357 mutation. FIG. 8D shows results from BC96 which contains both a K370R mutation in Domain B and an E357W mutation in Domain G.

Figure 9:
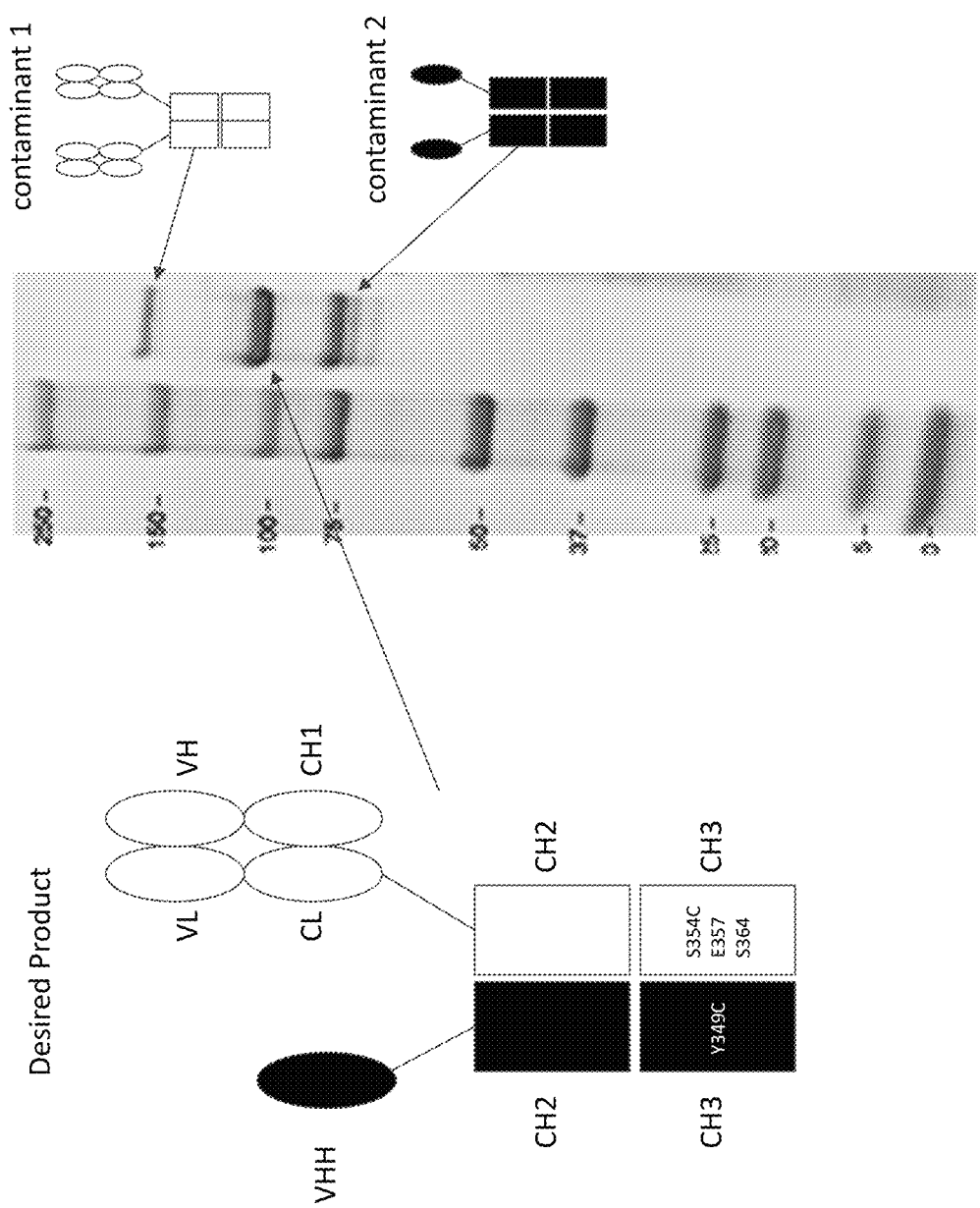

FIG. 9 presents a schematic of the construct created to evaluate the degree of orthogonality imparted by individual mutations. A representative SDS-PAGE gel showing bands corresponding to the desired product and contaminants is shown along with schematics of the homodimer contaminants.

Figure 10A:
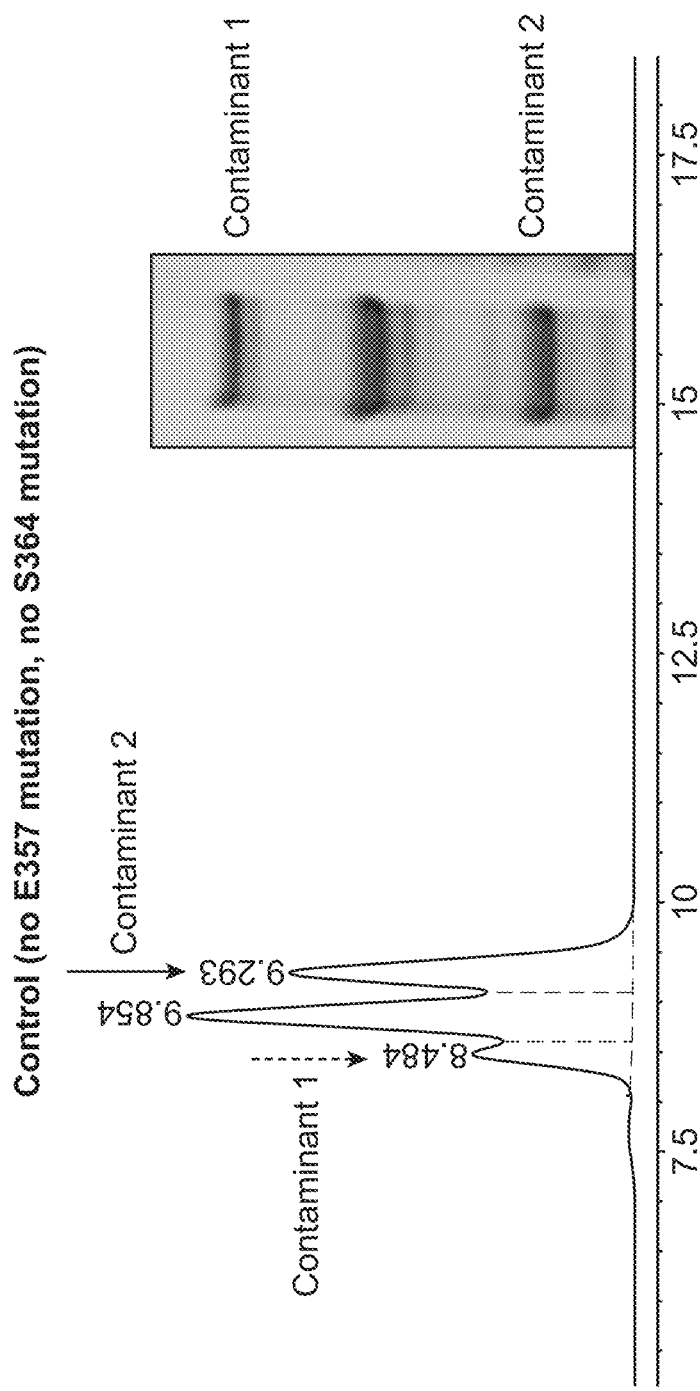
Figure 10B:
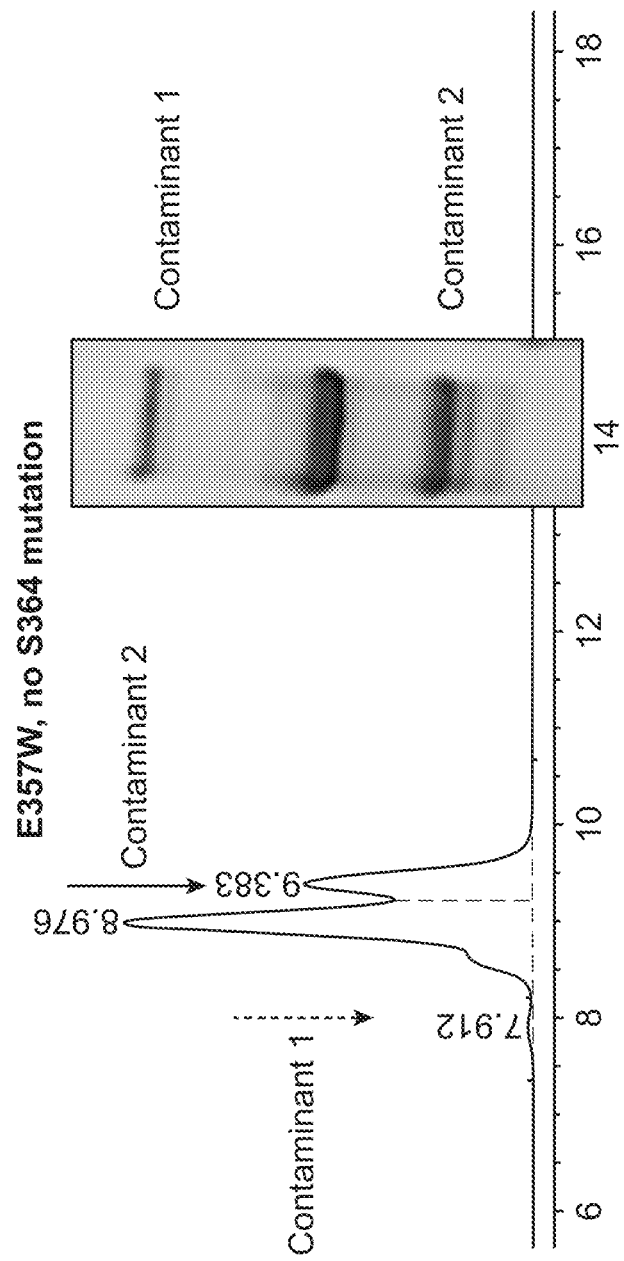
Figure 10C:
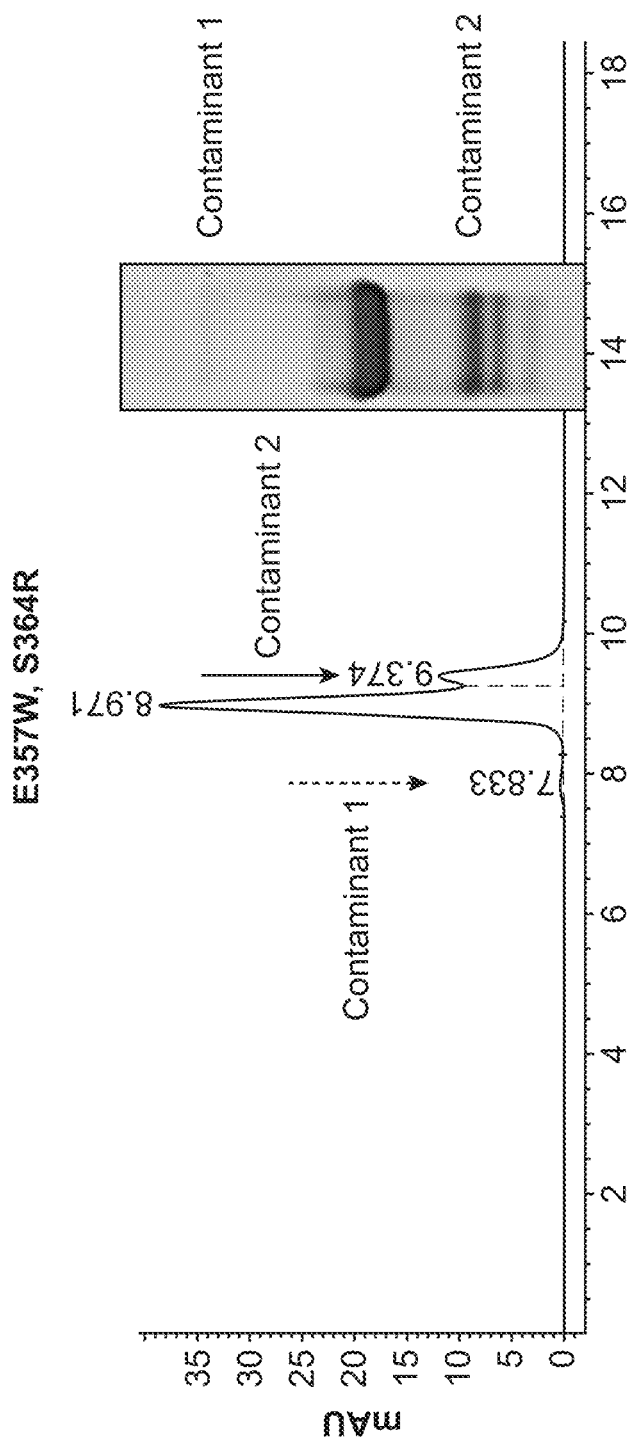

FIGS. 10A-10C show results of size exclusion chromatography (SEC) and SDS-PAGE analysis following Protein A purification of various constructs. FIG. 10A shows results from a construct in which a first CH3 domain contains an S354C mutation and a second opposing CH3 domain contains a Y349C mutation. FIG. 10B shows results from a construct in which a first CH3 domain contains S354C and E357W mutations and a second opposing CH3 domain contains a Y349C mutation. FIG. 10C shows results from a construct in which a first CH3 domain contains S354C, E357W, and S364R mutations and a second opposing CH3 domain contains a Y349C mutation.

Figure 11A:
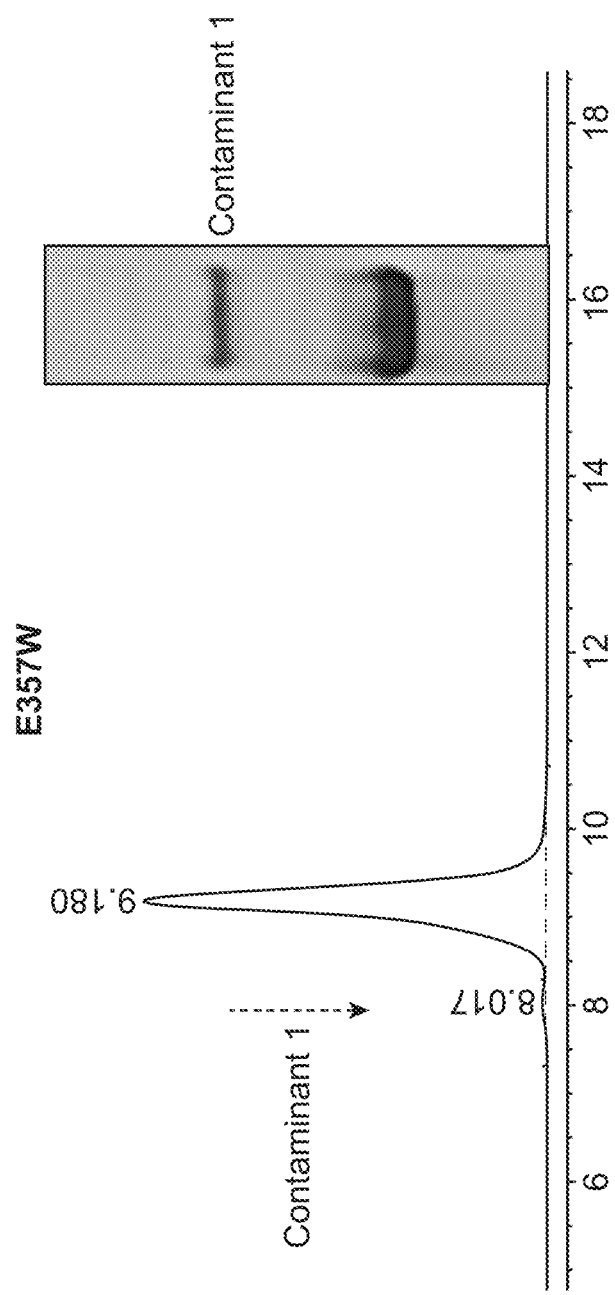
Figure 11B:
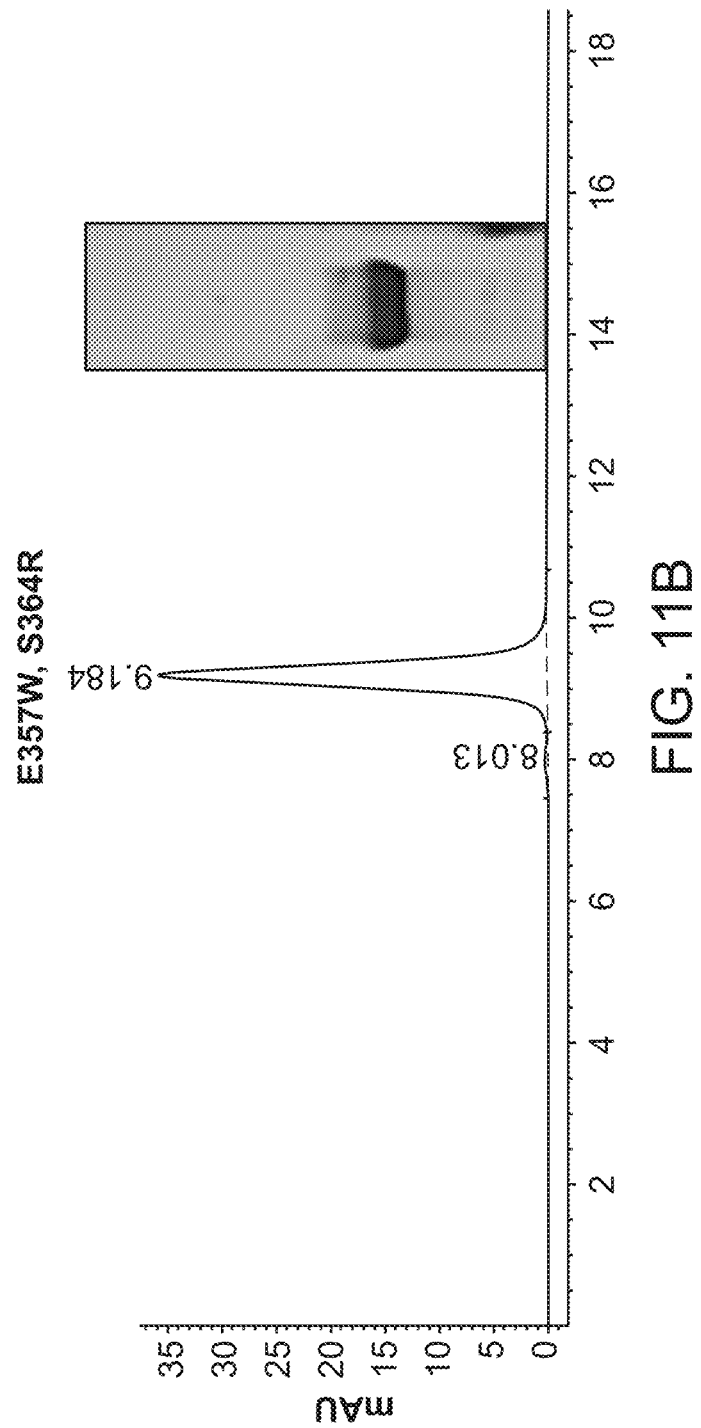

FIGS. 11A-11B show results of SEC and SDS-PAGE analysis following CH1 purification of various constructs. FIG. 11A shows results from a construct in which a first CH3 domain contains S354C and E357W mutations and a second opposing CH3 domain contains a Y349C mutation. FIG. 11B shows results from a construct in which a first CH3 domain contains S354C, E357W, and S364R mutations and a second opposing CH3 domain contains a Y349C mutation.

6. DETAILED DESCRIPTION OF THE INVENTION

6.1. Definitions

Unless otherwise defined herein, all technical and scientific terms used herein have the meaning commonly understood by a person skilled in the art to which this invention pertains.

As used herein, the following terms have the meanings ascribed to them below.

By "antigen binding site" ("ABS") is meant a region of an antibody construct that specifically recognizes or binds to a given antigen or epitope. An ABS, and the antibody construct comprising such ABS, is said to "recognize" the epitope (or more generally, the antigen) to which the ABS specifically binds, and the epitope (or more generally, the antigen) is said to be the "recognition specificity" or "binding specificity" of the ABS.

The ABS is said to bind to its specific antigen or epitope with a particular affinity. As described herein, "affinity" refers to the strength of interaction of non-covalent intermolecular forces between one molecule and another. The affinity, i.e. the strength of the interaction, can be expressed as a dissociation equilibrium constant ($K_D$), wherein a lower $K_D$ value refers to a stronger interaction between molecules. $K_D$ values of antibody constructs are measured by methods well known in the art including, but not limited to, bio-layer interferometry (e.g. Octet/FORTEBIO®), surface plasmon resonance (SPR) technology (e.g.) Biacore®, and cell binding assays. Unless otherwise specified, for purposes herein affinities are dissociation equilibrium constants measured by bio-layer interferometry using Octet/FORTEBIO®.

"Specific binding," as used herein, refers to an affinity between an ABS and its cognate antigen or epitope in which the $K_D$ value is below $10^{-6}$M, $10^{-7}$M, $10^{-8}$M, $10^{-9}$M, or $10^{-10}$M.

The number of ABSs in an antibody construct as described herein defines the "valency" of the antibody construct. An antibody construct having a single ABS is "monovalent". An antibody construct having a plurality of ABSs is said to be "multivalent". A multivalent antibody construct having two ABSs is "bivalent." A multivalent antibody construct three ABSs is "trivalent." A multivalent antibody construct having four ABSs is "tetravalent."

In various multivalent embodiments of antibody constructs, all of the plurality of ABSs have the same recognition specificity. Such a construct is a "monospecific" "multivalent" antibody construct. In other multivalent embodiments, at least two of the plurality of ABSs have different recognition specificities. Such antibody constructs are multivalent and "multispecific". In multivalent embodiments in which the ABSs collectively have two recognition specificities, the binding molecule is "bispecific." In multivalent embodiments in which the ABSs collectively have three recognition specificities, the binding molecule is "trispecific."

In multivalent embodiments in which the ABSs collectively have a plurality of recognition specificities for different epitopes present on the same antigen, the antibody construct is "multiparatopic." Multivalent embodiments in which the ABSs collectively recognize two epitopes on the same antigen are "biparatopic."

In various multivalent embodiments, multivalency of the antibody construct improves the avidity of the binding molecule for a specific target. As described herein, "avidity" refers to the overall strength of interaction between two or more molecules, e.g. a multivalent binding molecule for a specific target, wherein the avidity is the cumulative strength of interaction provided by the affinities of multiple ABSs. Avidity can be measured by the same methods as those used to determine affinity, as described above. In certain embodiments, the avidity of a binding molecule for a specific target is such that the interaction is a specific binding interaction, wherein the avidity between two molecules has a $K_D$ value below $10^{-6}$M, $10^{-7}$M, $10^{-8}$M, $10^{-9}$M, or $10^{-10}$M. In certain embodiments, the avidity of a binding molecule for a specific target has a $K_D$ value such that the interaction is a specific binding interaction, wherein the one or more affinities of individual ABSs do not have has a $K_D$ value that qualifies as specifically binding their respective antigens or epitopes on their own. In certain embodiments, the avidity is the cumulative strength of interaction provided by the affinities of multiple ABSs for separate antigens on a shared specific target or complex, such as separate antigens found on an individual cell. In certain embodiments, the avidity is the cumulative strength of interaction provided by the affinities of multiple ABSs for separate epitopes on a shared individual antigen.

"B-Body," as used herein, refers to antibody constructs as shown in FIG. 2, comprising a first and a second polypeptide chain, wherein: (a) the first polypeptide chain comprises a domain A, a domain B, a domain D, and a domain E, wherein the domains are arranged, from N-terminus to C-terminus, in a A-B-D-E orientation, and wherein domain A has a VL amino acid sequence, domain B has a CH3 amino acid sequence, domain D has a CH2 amino acid sequence, and domain E has a constant region domain amino acid sequence; (b) the second polypeptide chain comprises a domain F and a domain G, wherein the domains are arranged, from N-terminus to C-terminus, in a F-G orientation, and wherein domain F has a VH amino acid sequence and domain G has a CH3 amino acid sequence; and (c) the first and the second polypeptides are associated through an interaction between the A and the F domains and an interaction between the B and the G domains to form the antibody construct. B-bodies are described in more detail in US 2018/0118811 and WO 2019/204522, the disclosures of which are incorporated by reference in their entireties herein.

"Orthogonal modifications" or synonymously "orthogonal mutations" as described herein are one or more engineered mutations in an amino acid sequence of an antibody domain that alter the affinity of binding of a first domain having an orthogonal modification for a second domain having a complementary orthogonal modification, as compared to binding of the first and second domains in the absence of the orthogonal modifications. In some embodiments, the orthogonal modifications decrease the affinity of binding of the first domain having the orthogonal modification for the second domain having the complementary orthogonal modification, as compared to binding of the first and second domains in the absence of the orthogonal modifications. In some embodiments, the orthogonal modifications do not alter the affinity of binding of the first domain having the orthogonal modification for the second domain having the complementary orthogonal modification, as compared to binding of the first and second domains in the absence of the orthogonal modifications. In preferred embodiments, the orthogonal modifications increase the affinity of binding of the first domain having the orthogonal modification for the second domain having the complementary orthogonal modification, as compared to binding of the first and second domains in the absence of the orthogonal modifications. In certain preferred embodiments, the orthogonal modifications decrease the affinity of a domain having the orthogonal modifications for a domain lacking the complementary orthogonal modifications.

In particular embodiments, orthogonal modifications include, but are not limited to, engineered disulfide bridges, knob-in-hole mutations, and charge-pair mutations, as described in greater detail below. In particular embodiments, orthogonal modifications include a combination of orthogonal modifications selected from, but not limited to, engineered disulfide bridges, knob-in-hole mutations, and charge-pair mutations.

6.2. Other Interpretational Conventions

Unless otherwise specified, all references to "sequences" herein are to amino acid sequences. By "endogenous sequence" or "native sequence" is meant any sequence, including nucleic acid and amino acid sequences as context dictates, which originates from an organism, tissue, or cell and has not been artificially modified or mutated.

Unless otherwise specified, antibody constant region residue numbering is according to the Eu index as described at imgt.org which is hereby incorporated by reference in its entirety, and identifies the residue according to its location in an endogenous constant region sequence regardless of the residue's physical location within a chain of the antibody constructs described herein.

Unless otherwise specified, all references to complementarity determining regions (CDRs) are Kabat-defined CDRs.

The terms "first", "second", "third", "fourth", etc., when used with respect to polypeptide chains (e.g., a "first" polypeptide chain, a "second" polypeptide chain, etc. or polypeptide "chain 1," "chain 2," etc.) are used herein as a unique identifier for specific polypeptide chains that form a multimeric molecule, and are not intended to connote order or quantity of the different polypeptide chains within the antibody construct.

The terms "first", "second", "third", "fourth", etc., when used with respect to CH3 domains are used to designate specific domains, and are not intended to connote order or quantity of the domains.

In this disclosure, "comprises," "comprising," "containing," "having," "includes," "including," and linguistic variants thereof have the meaning ascribed to them in U.S. Patent law, permitting the presence of additional components beyond those explicitly recited.

Ranges provided herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless specifically stated or apparent from context, as used herein the term "or" is understood to be inclusive. Unless specifically stated or apparent from context, as used herein, the terms "a", "an", and "the" are understood to be singular or plural.

Unless specifically stated or otherwise apparent from context, as used herein the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise specified, "about" means within 10% of the stated value.

6.3. Heterodimeric Proteins

In a first aspect, heterodimeric proteins are provided. The heterodimeric proteins comprise a first polypeptide chain and a second polypeptide chain, wherein
a) the first polypeptide chain comprises a first CH3 domain and the second polypeptide chain comprises a second CH3 domain,
b) Y349 of the first CH3 domain is substituted with cysteine (C) (Y349C),
c) S354 of the second CH3 domain is substituted with cysteine (C) (S354C), and
d) E357 of the second CH3 domain is substituted with a hydrophobic or aromatic amino acid, wherein the positions are numbered according to the Eu index.

In various embodiments, the hydrophobic amino acid residue is selected from the group consisting of: alanine (A), isoleucine (I), leucine (L), methionine (M), proline (P), and valine (V). In various embodiments, the aromatic amino acid residue is selected from the group consisting of: histidine (H), tryptophan (W), phenylalanine (F), and tyrosine (Y).

In certain embodiments, E357 of the second CH3 domain is substituted with a hydrophobic amino acid. In a particular embodiment, the hydrophobic amino acid residue is methionine (M) (E357M).

In certain embodiments, E357 of the second CH3 domain is substituted with an aromatic amino acid. In particular embodiments, the aromatic amino acid residue is tryptophan (W) (E357W).

6.3.1. CH3 Domains

The CH3 domains of the heterodimeric proteins described herein have amino acid sequences derived from domains that are naturally positioned at the C-terminus of an antibody heavy chain, into which the mutations described above are engineered.

In a variety of embodiments, the CH3 sequences are mammalian sequences, including, but not limited to, mouse, rat, hamster, rabbit, canine, feline, camel, donkey, goat, and human sequences. In a preferred embodiment, the CH3 sequences are human sequences. In certain embodiments, the CH3 sequences are from an IgA1, IgA2, IgD, IgE, IgM, IgG1, IgG2, IgG3, IgG4 isotype. In specific embodiments, the CH3 sequences are from an IgG isotype. In a preferred embodiment, the CH3 sequences are from an IgG1 isotype. In some embodiments, the CH3 sequence is from an IgA isotype.

In certain embodiments, the CH3 sequences are CH4 sequences from an IgE or IgM isotype.

In certain embodiments, the CH3 sequences are endogenous sequences. In particular embodiments, the CH3 sequence is UniProt accession number P01857 amino acids 224-330. In various embodiments, a CH3 sequence is a segment of an endogenous CH3 sequence. In particular embodiments, a CH3 sequence has an endogenous CH3 sequence that lacks the N-terminal amino acids G224 and Q225. In particular embodiments, a CH3 sequence has an endogenous CH3 sequence that lacks the C-terminal amino acids P328, G329, and K330. In particular embodiments, a CH3 sequence has an endogenous CH3 sequence that lacks both the N-terminal amino acids G224 and Q225 and the C-terminal amino acids P328, G329, and K330.

In certain embodiments, the CH3 sequences are engineered to reduce immunogenicity by replacing specific amino acids of one allotype with those of another allotype (referred to herein as isoallotype mutations), as described in more detail in Stickler et al. (Genes Immun. 2011 Apr; 12(3): 213-221), which is herein incorporated by reference for all that it teaches. In particular embodiments, specific amino acids of the G1m1 allotype are replaced. In a preferred embodiment, isoallotype mutations D356E and L358M are made in the CH3 sequence.

In some embodiments, there are no additional engineered mutations in the first or second CH3 domains. In some embodiments, the CH3 sequences are endogenous sequences that have one or more engineered mutations additional to those described above, as described below.

6.3.2. Additional Engineered Orthogonal Mutations in the CH3 Domain

In some embodiments, there is at least one additional orthogonal mutation engineered into the first and/or second CH3 domain.

6.3.2.1 Cascade Mutations

In various embodiments, the first and/or second CH3 domain further comprises a mutation newly made possible by the E357 mutation, such as an E357W mutation (a "cascade" mutation).

In some embodiments, the CH3 domain opposite that containing an E357 mutation further comprises a mutation in K370. In various embodiments, the lysine (K) is mutated to A, D, E, F, G, H, I, L, M, N, P, Q, R, S, T, V, W, or Y. In particular embodiments, the lysine (K) is mutated to D, E, F, H, M, N, Q, R, S, T, W, or Y. In particular embodiments, the mutation is K370R.

In some embodiments, the CH3 domain that contains an E357 mutation further comprises a mutation in 5364. In various embodiments, the serine (S) is mutated to A, D, E, F, G, H, I, K, L, M, N, P, Q, R, T, V, W, or Y. In particular embodiments, the serine is mutated to A, D, E, H, K, L, N, Q, R, T, W or Y. In a preferred embodiment, the serine is mutated to R.

In some embodiments, the CH3 domain opposite that containing an E357 mutation further comprises a mutation in K370 and the domain that contains the E357 mutation further comprises a mutation in S364. In various embodiments, the K370 is mutated to D, E, F, H, M, N, Q, R, S, T, W, or Y. In particular embodiments, the mutation is K370R. In various embodiments S364 is mutated to A, D, E, H, K, L, N, Q, R, T, W or Y.

6.3.2.2 Knob-In-Hole

In various embodiments, the first and second CH3 domains further comprise orthogonal knob-in-hole ("K-I-H") mutations.

As used herein, knob-in-hole mutations are mutations that change the steric features of a first domain's surface such that the first domain will preferentially associate with a second domain having complementary steric mutations relative to association with domains without the complementary steric mutations. Knob-in-hole mutations are described in greater detail in U.S. Pat. Nos. 5,821,333 and 8,216,805, each of which is incorporated herein in its entirety.

In some embodiments, the at least one additional engineered mutation is a knob mutation in the first CH3 domain and a hole mutation in the second CH3 domain. In some embodiments, there is a hole mutation in the first CH3 domain and a knob mutation in the second CH3 domain.

In certain embodiments, the knob mutation is T366W or T366Y.

In certain embodiments, the hole mutation is selected from T366S, L368A, F405T, Y407V, or Y407T. In a specific embodiment, the hole mutation is F405T.

In certain embodiments, the knob-in-hole mutations are a T366W mutation in the first CH3 domain and a Y407A mutation in the second CH3 domain. In certain embodiments, the knob-in-hole mutations are a T366W mutation in the second CH3 domain and a Y407A mutation in the first CH3 domain.

In certain embodiments, the knob-in-hole mutations are a T366Y mutation in the first CH3 domain and a Y407T mutation in the second domain. In certain embodiments, the knob-in-hole mutations are a T366Y mutation in the second CH3 domain, and a Y407T mutation in the first domain.

In certain embodiments, the knob-in-hole mutations are a T394W in the first CH3 domain, and F405A in the second CH3 domain. In certain embodiments, the knob-in-hole mutations are a T394W in the second CH3 domain, and F405A in the first CH3 domain.

In certain embodiments, the knob-in-hole mutations are a T366Y mutation and a F405A in the first CH3 domain and a T394W mutation and a Y407T mutation in the second CH3 domain. In certain embodiments, the knob-in-hole mutations are a T366Y mutation and a F405A in the second CH3 domain and a T394W mutation and a Y407T mutation in the first CH3 domain.

6.3.2.3 Engineered Charge Pair

In various embodiments, the first and second CH3 domains further comprise orthogonal charge-pair mutations.

As used herein, charge-pair mutations are mutations that affect the charge of an amino acid in a domain's surface such that the domain will preferentially associate with a second domain having complementary charge-pair mutations relative to association with domains without the complementary charge-pair mutations. In certain embodiments, charge-pair mutations improve orthogonal association between specific domains. Charge-pair mutations are described in greater detail in U.S. Pat. Nos. 8,592,562; 9,248,182; and 9,358,286, each of which is incorporated herein by reference herein in its entirety.

In certain embodiments, the charge-pair mutations are a T366K mutation in the first CH3 domain and a L351D mutation in the second CH3 domain. In certain embodiments, the charge-pair mutations are a T366K mutation in the second CH3 domain and a L351D mutation in the first CH3 domain.

6.4. Antibody Constructs

6.4.1. Variable Domains

In various embodiments, at least one of the first and second polypeptide chains of the heterodimeric protein further comprises an immunoglobulin variable domain.

In some embodiments, both the first and second polypeptide chain further comprises an immunoglobulin variable domain.

In some embodiments, both the first and second polypeptide chains comprises a $V_H$ domain. In some embodiments, both the first and second polypeptide chains comprises a $V_L$ domain.

In some embodiments, the first polypeptide chain comprises a $V_H$ domain and the second polypeptide chain comprises a $V_L$ domain, or the first polypeptide chain comprises a $V_L$ domain and the second polypeptide chain comprises a $V_H$ domain. In these embodiments, the variable domains of the first and second polypeptides associate to form a first antigen binding site (ABS) and the heterodimeric protein is an antibody construct.

In certain antibody constructs, the polypeptide chain comprising the VH domain further comprises a CH2 domain and a third CH3 domain, wherein the domains are ordered from N terminus to C terminus, a) $V_H$—first CH3—CH2—third CH3,
b) $V_H$—second CH3-CH2-third CH3,
c) $V_H$—third CH3—CH2—first CH3, or
d) $V_H$—third CH3—CH2—second CH3.

In particular embodiments, the domains of the polypeptide chain comprising the $V_H$ domain are ordered, from N terminus to C terminus,
a) $V_H$—first CH3—CH2—third CH3, or
b) $V_H$—second CH3—CH2—third CH3.

In certain antibody construct embodiments, the polypeptide chain comprising the VL domain further comprises a CH2 domain and a third CH3 domain. In particular embodiments, with reference to FIG. 2, the domains are ordered, from N terminus to C terminus,

|    | domain A | — | domain B    | — | domain D | — | domain E      |
|----|----------|---|-------------|---|----------|---|---------------|
| a) | $V_L$    | — | first CH3   | — | CH2      | — | third CH3, or |
| b) | $V_L$    | — | second CH3  | — | CH2      | — | third CH3, or |
| c) | $V_L$    | — | third CH3   | — | CH2      | — | first CH3, or |
| d) | $V_L$    | — | third CH3   | — | CH2      | — | second CH3.   |

In particular embodiments, with reference to FIG. 2, the domains of the polypeptide chain comprising the $V_L$ domain are ordered, from N terminus to C terminus:

|    | domain A | — | domain B   | — | domain D | — | domain E      |
|----|----------|---|------------|---|----------|---|---------------|
| a) | $V_L$    | — | first CH3  | — | CH2      | — | third CH3, or |
| b) | $V_L$    | — | second CH3 | — | CH2      | — | third CH3.    |

In particular embodiments, with reference to FIG. 2, the domains of the polypeptide chain comprising the $V_L$ domain and the polypeptide chain comprising the $V_H$ domain are respectively ordered, from N terminus to C terminus:

| a) first polypeptide chain | | | | | | |
|---|---|---|---|---|---|---|
| domain A | — | domain B | — | domain D | — | domain E |
| $V_L$ | — | first CH3 | — | CH2 | — | third CH3 |
| second polypeptide chain | | | | | | |
| domain F | — | | | domain G | | |
| $V_H$ | — | | | second CH3 | | | or

| b) first polypeptide chain | | | | | | |
|---|---|---|---|---|---|---|
| domain A | — | domain B | — | domain D | — | domain E |
| $V_L$ | — | second CH3 | — | CH2 | — | third CH3 |
| second polypeptide chain | | | | | | |
| domain F | — | | | domain G | | |
| $V_H$ | — | | | first CH3. | | |

In various embodiments, with reference to FIG. 2, the antibody construct further comprises a third polypeptide chain and a fourth polypeptide chain, wherein:

(a) the third polypeptide chain comprises a domain H, a domain I, a domain J, and a domain K, wherein the domains are arranged, from N-terminus to C-terminus, in a H-I-J-K orientation, and wherein domain H has a variable region domain amino acid sequence, domain I has a constant region domain amino acid sequence, domain J has a CH2 amino acid sequence, and K has a constant region domain amino acid sequence;

(b) the fourth polypeptide chain comprises a domain L and a domain M, wherein the domains are arranged, from N-terminus to C-terminus, in a L-M orientation, and wherein domain L has a variable region domain amino acid sequence and domain M has a constant region domain amino acid sequence;

(c) the third and the fourth polypeptides are associated through an interaction between the H and the L domains, which form a second antigen binding site (ABS) and an interaction between the I and the M domains; and (d) the first and the third polypeptides are associated through an interaction between the D and the J domains and an interaction between the E and the K domains.

In particular embodiments, domain H is a $V_L$ domain; domain I is a CL domain; domain J is a CH2 domain; and domain K is a fourth CH3 domain. In specific embodiments, domain L is a $V_H$ domain; and domain M is a CH1 domain.

In particular embodiments, domain A has a $V_L$ antibody domain sequence and domain F has a $V_H$ antibody domain sequence. In some embodiments, domain A has a $V_H$ antibody domain sequence and domain F has a $V_L$ antibody domain sequence.

In some embodiments, the antibody construct comprises a native antibody architecture, wherein domains A and H comprise $V_H$ amino acid sequences, domains F and L comprise $V_L$ amino acid sequences, domains B and I comprise CH1, domains G and M comprise CL, domains D and J comprise CH2, and domains E and K comprise CH3.

In some embodiments, the antibody construct is a B-Body™. B-Body™ antibody constructs are described in US 2018/0118811 and WO 2019/204522, the disclosures of which are incorporated herein by reference in their entireties, with specific embodiments further described below.

In some embodiments, the antibody construct is a CrossMab™. CrossMab™ antibodies are described in U.S. Pat. Nos. 8,242,247; 9,266,967; and 8,227,577, U.S. Patent Application Pub. No. 20120237506, U.S. Patent Application Pub. No. US20090162359, WO2016016299, WO2015052230, each of which is hereby incorporated in its entirety by reference. In some embodiments, the antibody construct is a bivalent, bispecific antibody, comprising: a) the light chain and heavy chain of an antibody specifically binding to a first antigen; and b) the light chain and heavy chain of an antibody specifically binding to a second antigen, wherein constant domains CL and CH1 from the antibody specifically binding to a second antigen are replaced by each other.

In some embodiments, the antibody construct is an antibody having a general architecture described in U.S. Pat. No. 8,871,912 and WO 2016/087650, each of which is hereby incorporated in its entirety by reference. In some embodiments, the antibody construct is a domain-exchanged antibody comprising a light chain (LC) composed of VL-CH3, and a heavy chain (HC) comprising VH-CH3-CH2-CH3, wherein the VL-CH3 of the LC dimerizes with the VH-CH3 of the HC thereby forming a domain-exchanged LC/HC dimer comprising a CH3LC/CH3HC domain pair.

In some embodiments, the antibody construct is as described in WO 2017/011342, which is hereby incorporated in its entirety by reference. In some embodiments, the antibody construct is as described in WO 2006/093794, which is hereby incorporated in its entirety by reference.

6.4.1.1.1 VH Domains

In various embodiments, the $V_H$ domain has an amino acid sequence that is a mammalian sequence, including human sequences, humanized sequences, synthetic sequences, or combinations of human, non-human mammalian, and/or synthetic sequences. In various embodiments, the $V_H$ amino acid sequences are mutated sequences of naturally occurring sequences.

6.4.1.1.2 VL Domains

In various embodiments, the $V_L$ domain has an amino acid sequence that is a mammalian sequence, including human sequences, humanized sequences, synthetic sequences, or combinations of human, non-human mammalian, and/or synthetic sequences. In various embodiments, $V_L$ amino acid sequences are mutated sequences of naturally occurring sequences.

In certain embodiments, the $V_L$ amino acid sequence is a lambda (λ) light chain variable domain sequence. In certain embodiments, the $V_L$ amino acid sequence is a kappa (κ) light chain variable domain sequence.

6.4.1.1.3 Complementarity Determining Regions

The $V_H$ and $V_L$ domains of the antibody constructs described herein comprise highly variable sequences termed "complementarity determining regions" (CDRs), typically three CDRs (CDR1, CD2, and CDR3). In a variety of embodiments, the CDRs are mammalian sequences, including, but not limited to, mouse, rat, hamster, rabbit, camel, donkey, goat, and human sequences. In a preferred embodiment, the CDRs are human sequences. In various embodiments, the CDRs are naturally occurring sequences. In various embodiments, the CDRs are naturally occurring sequences that have been mutated to alter the binding affinity of the antigen-binding site for a particular antigen or epitope. In certain embodiments, the naturally occurring CDRs have been mutated in an in vivo host through affinity maturation and somatic hypermutation. In certain embodiments, the CDRs have been mutated in vitro through methods including, but not limited to, PCR-mutagenesis and chemical mutagenesis. In various embodiments, the CDRs are synthesized sequences including, but not limited to, CDRs obtained from random sequence CDR libraries and rationally designed CDR libraries.

6.4.1.1.4 Framework Regions and CDR Grafting

The $V_H$ and $V_L$ domains of the antibody constructs described herein comprise "framework region" (FR) sequences. FRs are generally conserved sequence regions that act as a scaffold for interspersed CDRs, typically in a FR1-CDR1-FR2-CDR2-FR3-CDR3-FR4 arrangement (from N-terminus to C-terminus). In a variety of embodiments, the FRs are mammalian sequences, including, but not limited to, mouse, rat, hamster, rabbit, canine, feline, camel, donkey, goat, and human sequences. In a preferred embodiment, the FRs are human sequences. In various embodiments, the FRs are naturally occurring sequences. In various embodiments, the FRs are synthesized sequences including, but not limited, rationally designed sequences.

In a variety of embodiments, the FRs and the CDRs are both from the same naturally occurring variable domain sequence. In a variety of embodiments, the FRs and the CDRs are from different variable domain sequences, wherein the CDRs are grafted onto the FR scaffold with the CDRs providing specificity for a particular antigen. In certain embodiments, the grafted CDRs are all derived from the same naturally occurring variable domain sequence. In certain embodiments, the grafted CDRs are derived from different variable domain sequences. In certain embodiments, the grafted CDRs are synthetic sequences including, but not limited to, CDRs obtained from random sequence CDR libraries and rationally designed CDR libraries. In certain embodiments, the grafted CDRs and the FRs are from the same species. In certain embodiments, the grafted CDRs and the FRs are from different species. In a preferred grafted CDR embodiment, an antibody is "humanized", wherein the grafted CDRs are non-human mammalian sequences including, but not limited to, mouse, rat, hamster, rabbit, camel, donkey, and goat sequences, and the FRs are human sequences. Humanized antibodies are discussed in more detail in U.S. Pat. No. 6,407,213, the entirety of which is hereby incorporated by reference for all it teaches. In various embodiments, portions or specific sequences of FRs from one species are used to replace portions or specific sequences of another species' FRs.

6.4.2. C111 and CL Domains

In various embodiments, at least one of the first and second polypeptide chains of the antibody construct further comprises an immunoglobulin CH1 domain. In various embodiments, at least one of the first and second polypeptide chains of the heterodimeric protein further comprises an immunoglobulin CL domain.

In various embodiments, the first polypeptide further comprises a CH1 domain and the second polypeptide further comprises a CL domain. In various embodiments, the second polypeptide further comprises a CH1 domain and the first polypeptide further comprises a CL domain.

In various embodiments, the CH1 sequences are endogenous sequences. In a variety of embodiments, the CH1 sequences are mammalian sequences, including, but not limited to mouse, rat, hamster, rabbit, camel, donkey, goat, and human sequences. In a preferred embodiment, the CH1 sequences are human sequences. In certain embodiments, the CH1 sequences are from an IgA1, IgA2, IgD, IgE, IgG1, IgG2, IgG3, IgG4, or IgM isotype. In a preferred embodiment, the CH1 sequences are from an IgG1 isotype. In preferred embodiments, the CH1 sequence is UniProt accession number P01857 amino acids 1-98.

The CL domains of the antibody constructs described herein are antibody light chain constant domains. In certain embodiments, the CL domains have sequences that are endogenous sequences. In a variety of embodiments, the CL sequences are mammalian sequences, including, but not limited to mouse, rat, hamster, rabbit, canine, feline, camel, donkey, goat, and human sequences. In a preferred embodiment, CL sequences are human sequences.

In certain embodiments, the CL amino acid sequences are lambda (λ) light chain constant domain sequences. In particular embodiments, the CL amino acid sequences are human lambda light chain constant domain sequences. In preferred embodiments, the lambda (λ) light chain sequence is UniProt accession number POCG04.

In certain embodiments, the CL amino acid sequences are kappa n light chain constant domain sequences. In a preferred embodiment, the CL amino acid sequences are human kappa n light chain constant domain sequences. In a preferred embodiment, the kappa light chain sequence is UniProt accession number P01834.

In certain embodiments, the CH1 sequence and the CL sequences are both endogenous sequences.

The CH1 domain folding is typically the rate limiting step in the secretion of IgG (Feige et al. Mol Cell. 2009 Jun 12;34(5):569-79; herein incorporated by reference in its entirety). Thus, purifying the antibody constructs described herein based on the rate limiting component of CH1-comprising polypeptide chains can provide a means to purify complete complexes from incomplete chains, e.g., purifying complexes having a limiting CH1 domain from complexes only having one or more non-CH1 comprising chains.

While the CH1 limiting expression may be a benefit in some aspects, as discussed, there is the potential for CH1 to limit overall expression of the complete antibody constructs. Thus, in certain embodiments, the expression of the polypeptide chain comprising the CH1 sequence(s) is adjusted to improve the efficiency of the antibody constructs forming complete complexes. In an illustrative example, the ratio of a plasmid vector constructed to express the polypeptide chain comprising the CH1 sequence(s) can be increased relative to the plasmid vectors constructed to express the other polypeptide chains. In another illustrative example, the polypeptide chain comprising the CH1 sequence(s) when compared to the polypeptide chain comprising the CL sequence(s) can be the smaller of the two polypeptide chains. In another specific embodiment, the expression of the polypeptide chain comprising the CH1 sequence(s) can be adjusted by controlling which polypeptide chain has the CH1 sequence(s). For example, engineering the antibody construct such that the CH1 domain is present in a two-domain polypeptide chain (e.g., the 4th polypeptide chain described herein), instead of the CH1 sequence's native position in a four-domain polypeptide chain (e.g., the 3rd polypeptide chain described herein), can be used to control the expression of the polypeptide chain comprising the CH1 sequence(s). However, in other aspects, a relative expression level of CH1 containing chains that is too high compared to the other chains can result in incomplete complexes the have the CH1 chain, but not each of the other chains. Thus, in certain embodiments, the expression of the polypeptide chain comprising the CH1 sequence(s) is adjusted to both reduce the formation incomplete complexes without the CH1 containing chain, and to reduce the formation incomplete complexes with the CH1 containing chain but without the other chains present in a complete complex.

In certain embodiments, the CH1 sequence and the CL sequences separately comprise respectively orthogonal modifications in endogenous CH1 and CL sequences, as discussed in greater detail below. Preferably, the orthogonal mutations in the CH1 sequence do not eliminate the specific binding interaction between the CH1 domain and CH1-specific binding reagent used for purification.

6.4.2.1 CH1 and CL Orthogonal Modifications

In certain embodiments, the CH1 sequence and the CL sequences further comprise respectively orthogonal modifications of endogenous CH1 and CL sequences. A CH1/CL orthogonal modification may affect the CH1/CL domain pairing via an interaction between a modified residue in the CH1 domain and a corresponding modified or unmodified residue in the CL domain.

In particular embodiments, the orthogonal modifications can be combined with amino acid substitutions that reduce immunogenicity, such as isoallotype mutations.

In other embodiments, one sequence of the CH1/CL pair comprises at least one modification while the other sequence of the CH1/CL pair does not comprise a modification in the respectively orthogonal amino acid position.

CH1 and CL sequences can also be portions thereof, either of an endogenous or modified sequence, such that a domain having the CH1 sequence, or portion thereof, can associate with a domain having the CH1 sequence, or portion thereof. Furthermore, the antibody construct having a portion of the CH1 sequences described herein can be bound by a CH1 binding reagent.

6.4.2.1.1 Exemplary CH1/CL Orthogonal Modifications: Engineered Disulfide Bridges Some embodiments of a CH1/CL orthogonal modification comprise an engineered disulfide bridge between engineered cysteines in CH1 and CL. Such engineered disulfide bridges may stabilize an interaction between the polypeptide comprising the modified CH1 and the polypeptide comprising the corresponding modified CL.

An orthogonal CH1/CL modification comprising an engineered disulfide bridge can comprise, by way of example only, a CH1 domain having an engineered cysteine at position 128, 129, 138, 141, 168, or 171, as numbered by the EU index. Such an orthogonal CH1/CL modification comprising an engineered disulfide bridge may further comprise, by way of example only, a CL domain having an engineered cysteine at position 116, 118, 119, 164, 162, or 210, as numbered by the EU index.

For example, a CH1/CL orthogonal modification may be selected from engineered cysteines at position 138 of the CH1 sequence and position 116 of the CL sequence, at position 128 of the CH1 sequence and position 119 of the CL sequence, or at position 129 of the CH1 sequence and position 210 of the CL sequence, as numbered and discussed in more detail in U.S. Pat. Nos. 8,053,562 and 9,527,927, each incorporated herein by reference in its entirety. In some embodiments, the CH1/CL orthogonal modification comprises an engineered cysteine at position 141 of the CH1 sequence and position 118 of the CL sequence, as numbered by the EU index.

In some embodiments, the CH1/CL orthogonal modification comprises an engineered cysteine at position 168 of the CH1 sequence and position 164 of the CL sequence, as numbered by the EU index. In some embodiments, the CH1/CL orthogonal modification comprises an engineered cysteine at position 128 of the CH1 sequence and position 118 of the CL sequence, as numbered by the EU index. In some embodiments, the CH1/CL orthogonal modification comprises an engineered cysteine at position 171 of the CH1 sequence and position 162 of the CL sequence, as numbered by the EU index. In some embodiments, the CL sequence is a CL-lambda sequence. In preferred embodiments, the CL sequence is a CL-kappa sequence. In some embodiments, the engineered cysteines are at position 128 of the CH1 sequence and position 118 of the CL Kappa sequence, as numbered by the EU index.

Table 1 below provides exemplary CH1/CL orthogonal modifications comprising an engineered disulfide bridge between CH1 and CL, numbered according to the EU index.

TABLE 1

Exemplary CH1/CL engineered disulfide bridges

| CH1 mutation | CL mutation |
| --- | --- |
| A141C | F118C |
| H168C | T164C |
| L128C | F118C |
| P171C | S162C |

In a series of preferred embodiments, the mutations that provide non-endogenous (engineered) cysteine amino acids are a F118C mutation in the CL sequence with a corresponding A141C in the CH1 sequence, or a F118C mutation in the CL sequence with a corresponding L128C in the CH1 sequence, a T164C mutation in the CL sequence with a corresponding H168C mutation in the CH1 sequence, or a S162C mutation in the CL sequence with a corresponding P171C mutation in the CH1 sequence, as numbered by the Eu index.

6.4.2.1.2 CH1/CL Orthogonal Modifications: Engineered Charge-Pair Mutations In a variety of embodiments, the orthogonal modifications in the CL sequence and the CH1 sequence are charge-pair mutations.

In specific embodiments the charge-pair mutations are a F118S, F118A or F118V mutation in the CL sequence with a corresponding A141L in the CH1 sequence, or a T129R mutation in the CL sequence with a corresponding K147D in the CH1 sequence, as numbered by the Eu index and described in greater detail in Bonisch et al. (Protein Engineering, Design & Selection, 2017, pp. 1-12), herein incorporated by reference for all that it teaches.

In some cases, the CH1/CL charge-pair mutations are a N138K mutation in the CL sequence with a corresponding G166D in the CH1 sequence, or a N138D mutation in the CL sequence with a corresponding G166K in the CH1 sequence, as numbered by the Eu index. In some embodiments, the charge-pair mutations are a P127E mutation in CH1 sequence with a corresponding E123K mutation in the corresponding CL sequence. In some embodiments, the charge-pair mutations are a P127K mutation in CH1 sequence with a corresponding E123 (not mutated) in the corresponding CL sequence.

Table 2 below provides exemplary CH1/CL orthogonal charged-pair modifications.

TABLE 2 exemplary CH1/CL orthogonal charged-pair modifications

| CH1 mutation | CL mutation |
|---|---|
| G166K | N138K |
| G166K | N138D |
| P127E | E123K |
| P127E | No mutation (E123) |
| P127K | E123K |
| P127K | No mutation (E123) |

6.4.2.1.3 Combinations of CH1/CL Orthogonal Modifications

In certain embodiments, the CH1 and CL domains of a single CH1/CL pair separately contain two or more respectively orthogonal modifications in endogenous CH1 and CL sequences. For instance, the CH1 and CL sequence may contain a first orthogonal modification and a second orthogonal modification in the endogenous CH1 and CL sequences. The two or more respectively orthogonal modifications in endogenous CH1 and CL sequences can be selected from any of the CH1/CL orthogonal modifications described herein.

In some embodiments, the first orthogonal modification is an orthogonal charge-pair mutation, and the second orthogonal modification is an orthogonal engineered disulfide bridge. In some embodiments, the first orthogonal modification is an orthogonal charge-pair mutation as described in Table 2, and the additional orthogonal modification comprise an engineered disulfide bridge selected from engineered cysteines at position 138 of the CH1 sequence and position 116 of the CL sequence, at position 128 of the CH1 sequence and position 119 of the CL sequence, or at position 129 of the CH1 sequence and position 210 of the CL sequence, as numbered and discussed in more detail in U.S. Pat. Nos. 8,053,562 and 9,527,927, each incorporated herein by reference in its entirety.

In some embodiments, the first orthogonal modification is an orthogonal charge-pair mutation as described in Table 2, and the additional orthogonal modification comprise an engineered disulfide bridge as described in Table 1. In some embodiments, the first orthogonal modification comprises an L128C mutation in the CH1 sequence and an F118C mutation in the CL sequence, and the second orthogonal modification comprises a modification of residue 166 in the same CH1 sequence and a modification of residue 138 in the same CL sequence.

In some embodiments, the first orthogonal modification comprises an L128C mutation in the CH1 sequence and an F118C mutation in the CL sequence, and the second orthogonal modification comprises a G166D mutation in the CH1 sequence and a N138K mutation in the CL sequence. In some embodiments, the first orthogonal modification comprises an L128C mutation in the CH1 sequence and an F118C mutation in the CL sequence, and the second orthogonal modification comprises a G166K mutation in the CH1 sequence and a N138D mutation in the CL sequence.

6.4.3. CH2 Domains

In various embodiments, at least one of the first and second polypeptide chains of the antibody construct further comprises a CH2 domain. In various embodiments, both the first polypeptide and the second polypeptide comprises a CH2 domain.

In some embodiments, the antibody construct has more than one paired set of CH2 domains. In various of these embodiments, a first set of paired CH2 domains has CH2 amino acid sequences from a first isotype and one or more orthologous sets of CH2 amino acid sequences from another isotype. The orthologous CH2 amino acid sequences, as described herein, are able to interact with CH2 amino acid sequences from a shared isotype but not significantly interact with the CH2 amino acid sequences from another isotype present in the antibody construct.

In particular embodiments, the first set of CH2 amino acid sequences is from the same isotype as the other non-CH2 domains in the antibody construct. In a specific embodiment, the first set has CH2 amino acid sequences from an IgG isotype and the one or more orthologous sets have CH2 amino acid sequences from an IgM or IgE isotype.

In certain embodiments, one or more of the sets of CH2 amino acid sequences are endogenous CH2 sequences. In other embodiments, one or more of the sets of CH2 amino acid sequences are endogenous CH2 sequences that have one or more mutations. In particular embodiments, the one or more mutations are orthogonal knob-hole mutations, orthogonal charge-pair mutations, or orthogonal hydrophobic mutations. Orthologous CH2 amino acid sequences useful for the antibody constructs described herein are described in more detail in international PCT applications WO2017/011342 and WO2017/106462, herein incorporated by reference in their entireties.

In particular embodiments, all sets of CH2 amino acid sequences are from the same species. In preferred embodiments, all sets of CH2 amino acid sequences are human CH2 amino acid sequences. In other embodiments, the sets of CH2 amino acid sequences are from different species.

6.4.4. Specific Bivalent Antibody Constructs

In various embodiments, the antibody construct has the architecture shown in FIG. 2.

6.4.4.1 Domain A

With reference to FIG. 2, in various embodiments of the antibody constructs described herein, domain A has a variable region domain amino acid sequence. In a preferred embodiment, domain A has a VL antibody domain sequence and domain F has a VH antibody domain sequence. In some embodiments, domain A has a VH antibody domain sequence and domain F has a VL antibody domain sequence.

In the antibody constructs described herein, the C-terminus of domain A is connected to the N-terminus of domain B. In certain embodiments, domain A has a VL amino acid sequence that is mutated at its C-terminus at the junction between domain A and domain B.

6.4.4.2 Domain B

With reference to FIG. 2, in various embodiments of the antibody constructs described herein, domain B has a constant region domain sequence.

In some embodiments, domain B has a CH3 sequence.

In certain embodiments, domain B has a CH3 sequence comprising "knob-in-hole" ("KIH") orthogonal mutations.

In certain embodiments, domain B has a CH3 sequence and either a S354C or a Y349C mutation that forms an engineered disulfide bridge with a CH3 domain containing an orthogonal mutation.

In certain embodiments, domain B has first CH3 domain sequence, wherein Y349 of the first CH3 domain is substituted with cysteine (C) (Y349C), wherein the positions are numbered according to the Eu index.

In certain embodiments, domain B has a second CH3 domain sequence, wherein S354 of the second CH3 domain is substituted with cysteine (C) (S354C), and E357 of the second CH3 domain is substituted with a hydrophobic or aromatic amino acid, wherein the positions are numbered according to the Eu index. In particular embodiments, the second CH3 domain has an E357W mutation.

In certain embodiments, domain B has a human IgG1 CH3 amino acid sequence with the following mutational changes: P343V; Y349C; and a tripeptide insertion, 445P, 446G, 447K. In other preferred embodiments, domain B has a human IgG1 CH3 sequence with the following mutational changes: T366K; and a tripeptide insertion, 445K, 446S, 447C. In still other preferred embodiments, domain B has a human IgG1 CH3 sequence with the following mutational changes: Y349C and a tripeptide insertion, 445P, 446G, 447K.

In certain embodiments, domain B has a human IgG1 CH3 sequence with a K447C mutation incorporated into an otherwise endogenous CH3 sequence.

In some embodiments, the constant region sequence is an orthologous CH2 sequence. In some embodiments, domain B has a CH2 sequence from IgE. In some embodiments, domain B has a CH2 sequence from IgM.

In some embodiments, for example wherein the valency of the binding molecule is three or greater than three, the constant region sequence is a CH1 or CL sequence. In some embodiments, domain B has a CH1 sequence. In some embodiments, the constant region sequence is a CL sequence. In some embodiments, the CH1 or CL sequence comprises one or more CH1 or CL orthogonal modifications described herein.

In the antibody constructs described herein, the N-terminus of domain B is connected to the C-terminus of domain A. In certain embodiments, domain B has a CH3 amino acid sequence that is mutated at its N-terminus at the junction between domain A and domain B.

In the antibody constructs described herein, the C-terminus of domain B is connected to the N-terminus of domain D. In certain embodiments, domain B has a CH3 amino acid sequence that is extended at the C-terminus at the junction between domain B and domain D.

In some embodiments, domain B comprises a human IgA CH3 sequence. In some embodiments, the IgA CH3 sequence comprises a CH3 linker sequence.

6.4.4.3 Domain D

With reference to FIG. 2, in various embodiments of the antibody constructs described herein, domain D has a constant region amino acid sequence.

In a preferred series of embodiments, domain D has a CH2 amino acid sequence. In certain embodiments, the CH2 sequences are endogenous sequences. In particular embodiments, the sequence is UniProt accession number P01857 amino acids 111-223. In a preferred embodiment, the CH2 sequences have an N-terminal hinge region peptide that connects the N-terminal variable domain-constant domain segment to the CH2 domain. In some embodiments, the CH2 sequence comprises one or more mutations that modulate effector function. In certain embodiments, the CH2 sequence comprises one or more mutations that reduce effector function. In some embodiments, the CH2 sequence comprises one or more mutations that modulate FcRN binding. In certain embodiments, the CH2 sequence comprises one or more mutations that reduce FcRN binding.

In the antibody constructs described herein, the N-terminus of domain D is connected to the C-terminus of domain B. In certain embodiments, domain B has a CH3 amino acid sequence that is extended at the C-terminus at the junction between domain D and domain B.

6.4.4.4 Domain E

With reference to FIG. 2, in various embodiments of the antibody constructs described herein, domain E has a constant region domain amino acid sequence.

In certain embodiments, the constant region sequence is a CH3 sequence.

In certain embodiments, domain E has a CH3 sequence comprising "knob-in-hole" ("KIH") orthogonal mutations.

In certain embodiments, domain E has a CH3 sequence and either a S354C or a Y349C mutation that forms an engineered disulfide bridge with a CH3 domain containing an orthogonal mutation.

In certain embodiments, domain E has first CH3 domain sequence, wherein Y349 of the first CH3 domain is substituted with cysteine (C) (Y349C).

In certain embodiments, domain E has a second CH3 domain sequence, wherein S354 of the second CH3 domain is substituted with cysteine (C) (S354C), and E357 of the second CH3 domain is substituted with a hydrophobic or aromatic amino acid, wherein the positions are numbered according to the Eu index. In particular embodiments, the second CH3 domain has an E357W mutation.

In certain embodiments, the constant region domain sequence is a CH1 sequence. In particular embodiments, the CH1 amino acid sequence of domain E is the only CH1 amino acid sequence in the binding molecule. In certain embodiments, the N-terminus of the CH1 domain is connected to the C-terminus of a CH2 domain.

In certain embodiments, the constant region sequence is a CL sequence. In certain embodiments, the N-terminus of the CL domain is connected to the C-terminus of a CH2 domain.

6.4.4.5 Domain F

With reference to FIG. 2, in various embodiments of the antibody constructs described herein, domain F has a variable region domain amino acid sequence. In a preferred embodiment, domain F has a VH antibody domain sequence. In some embodiments, domain F has a VL antibody domain sequence.

6.4.4.6 Domain G

With reference to FIG. 2, in various embodiments of the antibody constructs described herein, domain G has a constant region amino acid sequence.

In some embodiments, domain G has a CH3 amino acid sequence.

In certain embodiments, domain G has a human IgG1 CH3 sequence with the following mutational changes: S354C; and a tripeptide insertion, 445P, 446G, 447K. In some embodiments, domain G has a human IgG1 CH3 sequence with the following mutational changes: S354C; and 445P, 446G, 447K tripeptide insertion. In some preferred embodiments, domain G has a human IgG1 CH3 sequence with the following changes: L351D, and a tripeptide insertion of 445G, 446E, 447C.

In certain embodiments, domain G has a CH3 sequence comprising "knob-in-hole" ("KIH") orthogonal mutations.

In certain embodiments, domain G has a CH3 sequence and either a S354C or a Y349C mutation that forms an engineered disulfide bridge with a CH3 domain containing an orthogonal mutation.

In certain embodiments, domain G has first CH3 domain sequence, wherein Y349 of the first CH3 domain is substituted with cysteine (C) (Y349C).

In certain embodiments, domain G has a second CH3 domain sequence, wherein 5354 of the second CH3 domain is substituted with cysteine (C) (S354C), and E357 of the second CH3 domain is substituted with a hydrophobic or aromatic amino acid, wherein the positions are numbered according to the Eu index. In particular embodiments, the second CH3 domain has an E357W mutation.

In some embodiments, domain G has a human IgA CH3 sequence.

In some embodiments, domain G has a CL sequence.

In some embodiments, domain G has a CH2 sequence from IgE. In some embodiments, domain G has a CH2 sequence from IgM.

In particular embodiments, for example wherein the valency of the binding molecule is three or greater than three, the constant region sequence is a CH1 or CL sequence. In some embodiments wherein domain B is a CL sequence, domain G is a CH1 sequence. In some embodiments, the CH1 or CL sequence comprises one or more CH1 or Cl orthogonal modifications described herein.

In some embodiments, the C-terminus of domain G is connected to the N-terminus of domain D. In certain embodiments, domain G has a CH3 amino acid sequence that is extended at the C-terminus at the junction between domain G and domain D.

6.4.4.7 Domain H

With reference to FIG. 2, in various embodiments of the antibody constructs described herein, domain H has a variable region domain amino acid sequence. In a preferred embodiment, domain H has a VL antibody domain sequence. In some embodiments, domain H has a VH antibody domain sequence.

6.4.4.8 Domain I

With reference to FIG. 2, in various embodiments of the antibody constructs described herein, domain I has a constant region domain amino acid sequence.

In a series of preferred embodiments of the binding molecules, domain I has a CL amino acid sequence. In another series of embodiments, domain I has a CH1 amino acid sequence.

6.4.4.9 Domain J

With reference to FIG. 2, in various embodiments of the antibody constructs described herein, domain J has a CH2 amino acid sequence. In a preferred embodiment, the CH2 amino acid sequence has an N-terminal hinge region that connects domain J to domain I. In some embodiments, the CH2 sequence comprises one or more mutations that modulate effector function. In certain embodiments, the CH2 sequence comprises one or more mutations that reduce effector function. In some embodiments, the CH2 sequence comprises one or more mutations that modulate FcRN binding. In certain embodiments, the CH2 sequence comprises one or more mutations that reduce FcRN binding.

The C-terminus of domain J is connected to the N-terminus of domain K. In particular embodiments, domain J is connected to the N-terminus of domain K that has a CH1 amino acid sequence or CL amino acid sequence.

6.4.4.10 Domain K

With reference to FIG. 2, in various embodiments of the antibody constructs described herein, domain K has a constant region domain amino acid sequence.

In some embodiments, domain K has a CH3 sequence.

In certain embodiments, domain K has a CH3 sequence comprising "knob-in-hole" ("KIH") orthogonal mutations.

In certain embodiments, domain K has a CH3 sequence and either a S354C or a Y349C mutation that forms an engineered disulfide bridge with a CH3 domain containing an orthogonal mutation.

In certain embodiments, domain K has first CH3 domain sequence, wherein Y349 of the first CH3 domain is substituted with cysteine (C) (Y349C).

In certain embodiments, domain K has a second CH3 domain sequence, wherein 5354 of the second CH3 domain is substituted with cysteine (C) (S354C), and E357 of the second CH3 domain is substituted with a hydrophobic or aromatic amino acid, wherein the positions are numbered according to the Eu index. In particular embodiments, the second CH3 domain has an E357W mutation.

In some embodiments, knob-in-hole orthogonal mutations are combined with isoallotype mutations. In certain embodiments, the knob mutation is T366W or T366Y. In certain embodiments, the hole mutation is selected from T366S, L368A, F405T, Y407V, or Y407T. In a specific embodiment, the hole mutation is F405T.

In certain embodiments, the constant region domain sequence is a CH1 sequence. In particular embodiments, the CH1 amino acid sequence of domain K is the only CH1 amino acid sequence in the binding molecule. In certain embodiments, the N-terminus of the CH1 domain is connected to the C-terminus of a CH2 domain. In certain embodiments, the constant region sequence is a CL sequence. In certain embodiments, the N-terminus of the CL domain is connected to the C-terminus of a CH2 domain.

6.4.4.11 Domain L

With reference to FIG. 2, in various embodiments of the antibody constructs described herein, domain L has a variable region domain amino acid sequence. In a preferred embodiment, domain L has a $V_H$ antibody domain sequence. In some embodiments, domain L has a $V_L$ antibody domain sequence.

6.4.4.12 Domain M

With reference to FIG. 2, in various embodiments of the antibody constructs described herein, domain M has a constant region domain amino acid sequence. In a series of preferred embodiments, domain I has a CH1 amino acid sequence and domain M has a CL amino acid sequence. In another series of preferred embodiments, domain I has a CL amino acid sequence and domain M has a CH1 amino acid sequence.

6.4.4.13 Pairing of Domains A & F

In the antibody constructs illustrated in FIG. 2, a domain "A" VL or VH amino acid sequence and a cognate domain "F" $V_H$ or $V_L$ amino acid sequence are associated and form an antigen binding site (ABS). The A:F antigen binding site (ABS) is capable of specifically binding an epitope of an antigen.

In a variety of multivalent embodiments, the ABS formed by domains A and F (A:F) is identical in sequence to one or more other ABSs within the binding molecule and therefore has the same recognition specificity as the one or more other sequence-identical ABSs within the binding molecule.

In a variety of multivalent embodiments, the A:F ABS is non-identical in sequence to one or more other ABSs within the binding molecule. In certain embodiments, the A:F ABS has a recognition specificity different from that of one or more other sequence-non-identical ABSs in the binding molecule. In particular embodiments, the A:F ABS recognizes a different antigen from that recognized by at least one other sequence-non-identical ABS in the binding molecule. In particular embodiments, the A:F ABS recognizes a different epitope of an antigen that is also recognized by at least one other sequence-non-identical ABS in the binding molecule. In these embodiments, the ABS formed by domains A and F recognizes an epitope of antigen, wherein one or more other ABSs within the binding molecule recognizes the same antigen but not the same epitope.

6.4.4.14 Pairing of Domains B & G

In the antibody constructs illustrated in FIG. 2, a domain "B" constant region amino acid sequence and a domain "G" constant region amino acid sequence are associated.

In some embodiments, domain B and domain G have CH3 amino acid sequences.

In certain embodiments, domain B is a first CH3 domain and domain G is a second CH3 domain, wherein Y349 of the first CH3 domain is substituted with cysteine (C) (Y349C), S354 of the second CH3 domain is substituted with cysteine (C) (S354C), and E357 of the second CH3 domain is substituted with a hydrophobic or aromatic amino acid, wherein the positions are numbered according to the Eu index.

In certain embodiments, domain B is a second CH3 domain and domain G is a first CH3 domain, wherein Y349 of the first CH3 domain is substituted with cysteine (C) (Y349C), S354 of the second CH3 domain is substituted with cysteine (C) (S354C), and E357 of the second CH3 domain is substituted with a hydrophobic or aromatic amino acid, wherein the positions are numbered according to the Eu index.

In various embodiments, the amino acid sequences of the B and the G domains are identical. In certain of these embodiments, the sequence is an endogenous CH3 sequence. The sequence may be a CH3 sequence from human IgG1. The sequence may be a sequence from human IgA.

In a variety of embodiments, the amino acid sequences of the B and the G domains are different, and separately comprise respectively orthogonal modifications in an endogenous CH3 sequence, wherein the B domain interacts with the G domain, and wherein neither the B domain nor the G domain significantly interacts with a CH3 domain lacking the orthogonal modification.

In particular embodiments, it is desirable to reduce an undesired association of domains B or G containing CH3 sequences with domains E and K also containing CH3 sequences. In such cases, use of CH3 sequences from human IgA (IgA-CH3) in domains B and/or G may improve antibody assembly and stability by reducing such undesired associations. In some embodiments of a binding molecule wherein domains E and K comprise IgG-CH3 sequences, domains B and G comprise IgA-CH3 sequences.

6.4.4.15 Pairing of Domains E & K

In certain embodiments, domain E is a first CH3 domain and domain K is a second CH3 domain, wherein Y349 of the first CH3 domain is substituted with cysteine (C) (Y349C), S354 of the second CH3 domain is substituted with cysteine (C) (S354C), and E357 of the second CH3 domain is substituted with a hydrophobic or aromatic amino acid, wherein the positions are numbered according to the Eu index.

In certain embodiments, domain E is a second CH3 domain and domain K is a first CH3 domain, wherein Y349 of the first CH3 domain is substituted with cysteine (C) (Y349C), S354 of the second CH3 domain is substituted with cysteine (C) (S354C), and E357 of the second CH3 domain is substituted with a hydrophobic or aromatic amino acid, wherein the positions are numbered according to the Eu index.

In certain embodiments, the different sequences separately comprise respectively orthogonal modifications in an endogenous CH3 sequence, wherein the E domain interacts with the K domain, and wherein neither the E domain nor the K domain significantly interacts with a CH3 domain lacking the orthogonal modification. In certain embodiments, the orthogonal modifications include, but are not limited to, engineered disulfide bridges, knob-in-hole mutations, and charge-pair mutations. In particular embodiments, orthogonal modifications include a combination of orthogonal modifications selected from, but not limited to, engineered disulfide bridges, knob-in-hole mutations, and charge-pair mutations.

In particular embodiments, the orthogonal modifications can be combined with amino acid substitutions that reduce immunogenicity, such as isoallotype mutations.

In various embodiments, the amino acid sequences of the E and the K domains are identical.

6.4.4.16 Pairing of Domains H & L

In a variety of embodiments, domain H has a VL sequence and domain L has a VH sequence and domain "H" VL a domain "L" VH amino acid sequence are associated and form an antigen binding site (ABS). The H:L antigen binding site (ABS) is capable of specifically binding an epitope of an antigen.

In preferred embodiments, domain H has a VL amino acid sequence, domain I has a CL amino acid sequence, domain L has a VH amino acid sequence, and domain M has a CH1 amino acid sequence.

In a variety of embodiments, the amino acid sequences of the H domain and the L domain separately comprise respectively orthogonal modifications in an endogenous sequence, wherein the H domain interacts with the L domain, and wherein neither the H domain nor the L domain significantly interacts with a domain lacking the orthogonal modification. In a series of embodiments, the orthogonal mutations in the H domain are in a VL sequence and the orthogonal mutations in the L domain are in VH sequence. In specific embodiments, the orthogonal mutations are charge-pair mutations at the VH/VL interface. In preferred embodiments, the charge-pair mutations at the VH/VL interface are a Q39E in VH with a corresponding Q38K in VL, or a Q39K in VH with a corresponding Q38E in VL, as described in greater detail in Igawa et al. (Protein Eng. Des. Sel., 2010, vol. 23, 667-677), herein incorporated by reference in its entirety.

In certain embodiments, the interaction between the A domain and the F domain form a first antigen binding site specific for a first antigen, and the interaction between the H domain and the L domain form a second antigen binding site specific for a second antigen. In certain embodiments, the interaction between the A domain and the F domain form a first antigen binding site specific for a first antigen, and the interaction between the H domain and the L domain form a second antigen binding site specific for the first antigen.

6.4.4.17 Pairing of Domains I & M

In a variety of embodiments, domain I has a CL sequence and domain M has a CH1 sequence.

In a variety of embodiments, the amino acid sequences of the I domain and the M domain separately comprise respectively orthogonal modifications in an endogenous sequence, wherein the I domain interacts with the M domain, and wherein neither the I domain nor the M domain significantly interacts with a domain lacking the orthogonal modification. In a series of embodiments, the orthogonal mutations in the I domain are in a CL sequence and the orthogonal mutations in the M domain are in CH1 sequence.

6.4.4.18 Domain Junctions 6.4.4.18.1 Junctions Connecting VL and CH3 Domains

In a variety of embodiments, the amino acid sequence that forms a junction between the C-terminus of a VL domain and the N-terminus of a CH3 domain is an engineered sequence.

In certain embodiments, one or more amino acids are deleted or added in the C-terminus of the VL domain. In particular embodiments, A111 is deleted in the C-terminus of the VL domain. In certain embodiments, one or more amino acids are deleted or added in the N-terminus of the CH3 domain. In particular embodiments, P343 is deleted in the N-terminus of the CH3 domain. In particular embodiments, P343 and R344 are deleted in the N-terminus of the CH3 domain. In certain embodiments, one or more amino acids are deleted or added to both the C-terminus of the VL domain and the N-terminus of the CH3 domain. In particular embodiments, A111 is deleted in the C-terminus of the VL domain and P343 is deleted in the N-terminus of the CH3 domain. In a preferred embodiment, A111 and V110 are deleted in the C-terminus of the VL domain. In another preferred embodiment, A111 and V110 are deleted in the C-terminus of the VL domain and the N-terminus of the CH3 domain has a P343V mutation.

6.4.4.18.2 Junctions Connecting VH and CH3 Domains

In a variety of embodiments, the amino acid sequence that forms a junction between the C-terminus of a VH domain and the N-terminus of a CH3 domain is an engineered sequence.

In certain embodiments, one or more amino acids are deleted or added in the C-terminus of the VH domain. In particular embodiments, K117 and G118 are deleted in the C-terminus of the VH domain. In certain embodiments, one or more amino acids are deleted or added in the N-terminus of the CH3 domain. In particular embodiments, P343 is deleted in the N-terminus of the CH3 domain. In particular embodiments, P343 and R344 are deleted in the N-terminus of the CH3 domain. In particular embodiments, P343, R344, and E345 are deleted in the N-terminus of the CH3 domain. In certain embodiments, one or more amino acids are deleted or added to both the C-terminus of the VH domain and the N-terminus of the CH3 domain. In a preferred embodiment, T116, K117, and G118 are deleted in the C-terminus of the VH domain.

6.4.4.18.3 Junctions Connecting CH3 C-Terminus to CH2 N-terminus (Hinge)

In some embodiments of the antibody constructs described herein, the N-terminus of the CH2 domain has a "hinge" region amino acid sequence. As used herein, hinge regions are sequences of an antibody heavy chain that link the N-terminal variable domain-constant domain segment of an antibody and a CH2 domain of an antibody. In addition, the hinge region typically provides both flexibility between the N-terminal variable domain-constant domain segment and CH2 domain, as well as amino acid sequence motifs that form disulfide bridges between heavy chains (e.g. the first and the third polypeptide chains).

In a variety of embodiments, a CH3 amino acid sequence is extended at the C-terminus at the junction between the C-terminus of the CH3 domain and the N-terminus of a CH2 domain. In certain embodiments, a CH3 amino acid sequence is extended at the C-terminus at the junction between the C-terminus of the CH3 domain and a hinge region, which in turn is connected to the N-terminus of a CH2 domain. In a preferred embodiment, the CH3 amino acid sequence is extended by inserting a CH3 amino acid extension sequence ("CH3 linker sequence" or "CH3 linker"). In some embodiments, the CH3 amino acid extension sequence is followed by the DKTHT motif of an IgG1 hinge region. In some embodiments, the CH3 amino acid extension sequence is 3-10 amino acids in length. In some embodiments, the CH3 amino acid extension sequence is 3-8 amino acids in length. In some embodiments, the CH3 amino acid extension sequence is 3-6 amino acids in length.

In some embodiments, the CH3 amino acid extension sequence is a PGK tripeptide. In some embodiments, the CH3 amino acid extension sequence is an AGC tripeptide. In some embodiments, the CH3 amino acid extension sequence is a GEC tripeptide. In some embodiments, the CH3 amino acid extension sequence is AGKC. In some embodiments, the CH3 amino acid extension sequence is PGKC. In some embodiments, the CH3 amino acid extension sequence is AGKGC. In some embodiments, the CH3 amino acid extension sequence is AGKGSC.

In a particular embodiment, the extension at the C-terminus of the CH3 domain incorporates amino acid sequences that can form a disulfide bond with orthogonal C-terminal extension of another CH3 domain. In a preferred embodiment, the extension at the C-terminus of the CH3 domain incorporates a KSC tripeptide sequence that is followed by the DKTHT motif of an IgG1 hinge region that forms a disulfide bond with orthogonal C-terminal extension of another CH3 domain that incorporates a GEC motif of a kappa light chain.

In some embodiments of a binding molecule wherein domains B and G comprise CH3 amino acid sequences, domain B comprises a first CH3 linker sequence and domain G comprises a second CH3 linker sequence. In some embodiments, the first CH3 linker sequence associates with the second CH3 linker sequence by formation of a disulfide bridge between cysteine residues of the first and second CH3 linker sequences. In some embodiments, the first CH3 linker and the second CH3 linker are identical. In some embodiments, the first CH3 linker and second CH3 linker are non-identical. In some embodiments, the first CH3 linker and second CH3 linker differ in length by 1-6 amino acids. In some embodiments, the first CH3 linker and second CH3 linker differ in length by 1-3 amino acids.

In preferred embodiments, the first CH3 linker is AGC and the second CH3 linker is AGKGSC. In some embodiments, the first CH3 linker is AGKGC and the second CH3 linker is AGC. In some embodiments, the first CH3 linker is AGKGSC and the second CH3 linker is AGC. In some embodiments, the first CH3 linker is AGKC and the second CH3 linker is AGC.

6.4.4.18.4 Junctions Connecting CL C-Terminus and CH2 N-Terminus (Hinge)

In a variety of embodiments, a CL amino acid sequence is connected through its C-terminus to a hinge region, which in turn is connected to the N-terminus of a CH2 domain.

6.4.4.18.5 Junctions Connecting CH2 C-Terminus to Constant Region Domain

In a variety of embodiments, a CH2 amino acid sequence is connected through its C-terminus to the N-terminus of a constant region domain. In a preferred embodiment, the CH2 sequence is connected to a CH3 sequence via its endogenous sequence. In other embodiments, the CH2 sequence is connected to a CH1 or CL sequence. Examples discussing connecting a CH2 sequence to a CH1 or CL sequence are described in more detail in U.S. Pat. No. 8,242,247, which is hereby incorporated by reference in its entirety.

6.4.4.19 Bivalent Bispecific B-Body "BC1"

With reference to FIG. 2 and FIG. 3, in a series of embodiments, the antibody construct has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a T366K mutation and a C-terminal extension incorporating a KSC tripeptide sequence that is followed by the DKTHT motif of an IgG1 hinge region, domain D has a human IgG1 CH2 amino acid sequence, and domain E has human IgG1 CH3 amino acid with a S354C and T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a L351D mutation and a C-terminal extension incorporating a GEC amino acid disulfide motif; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, a D356E, a L358M, a T366S, a L368A, and a Y407V mutation; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 CH1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; (g) the first and the third polypeptides are associated through an interaction between the D and the J domains and an interaction between the E and the K domains to form the binding molecule; (h) domain A and domain F form a first antigen binding site specific for a first antigen; and (i) domain H and domain L form a second antigen binding site specific for a second antigen.

The orthogonal mutations described herein can be further engineered into the E:K paired domains of this construct.

6.4.4.20 Bivalent Bispecific B-Body "BC6"

With reference to FIG. 2 and FIG. 4, in a series of embodiments, the binding molecule has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a C-terminal extension incorporating a KSC tripeptide sequence that is followed by the DKTHT motif of an IgG1 hinge region, domain D has a human IgG1 CH2 amino acid sequence, and domain E has human IgG1 CH3 amino acid with a S354C and a T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a C-terminal extension incorporating a GEC amino acid disulfide motif; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, a D356E, a L358M, a T366S, a L368A, and a Y407V mutation; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; (g) the first and the third polypeptides are associated through an interaction between the D and the J domains and an interaction between the E and the K domains to form the binding molecule; (h) domain A and domain F form a first antigen binding site specific for a first antigen; and (i) domain H and domain L form a second antigen binding site specific for a second antigen.

The orthogonal mutations described herein can be further engineered into the E:K paired domains.

6.4.4.21 Bivalent Bispecific B-Body "BC28"

With reference to FIG. 2 and FIG. 5, in a series of embodiments, the binding molecule has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a Y349C mutation and a C-terminal extension incorporating a PGK tripeptide sequence that is followed by the DKTHT motif of an IgG1 hinge region, domain D has a human IgG1 CH2 amino acid sequence, and domain E has a human IgG1 CH3 amino acid with a S354C and a T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a S354C mutation and a C-terminal extension incorporating a PGK tripeptide sequence; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, a D356E, a L358M, a T366S, a L368A, and a Y407V; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 CH1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; (g) the first and the third polypeptides are associated through an interaction between the D and the J domains and an interaction between the E and the K domains to form the binding molecule; (h) domain A and domain F form a first antigen binding site specific for a first antigen; and (i) domain H and domain L form a second antigen binding site specific for a second antigen.

The orthogonal mutations described herein can be further engineered into the B:G paired domains or E:K paired domains.

6.4.4.22 Bivalent Bispecific B-Body "BC44"

With reference to FIG. 2 and FIG. 6, in a series of embodiments, the binding molecule has a first, second, third, and fourth polypeptide chain, wherein (a) the first polypeptide chain comprises a domain A, a domain B, a domain D, and a domain E, wherein the domains are arranged, from N-terminus to C-terminus, in a A-B-D-E orientation, and domain A has a first VL amino acid sequence, domain B has a human IgG1 CH3 amino acid sequence with a Y349C mutation, a P343V mutation, and a C-terminal extension incorporating a PGK tripeptide sequence that is followed by the DKTHT motif of an IgG1 hinge region, domain D has a human IgG1 CH2 amino acid sequence, and domain E has human IgG1 CH3 amino acid with a S354C mutation and a T366W mutation; (b) the second polypeptide chain has a domain F and a domain G, wherein the domains are arranged, from N-terminus to C-terminus, in a F-G orientation, and wherein domain F has a first VH amino acid sequence and domain G has a human IgG1 CH3 amino acid sequence with a S354C mutation and a C-terminal extension incorporating a PGK tripeptide sequence; (c) the third polypeptide chain has a domain H, a domain I, a domain J, and a domain K, wherein the domains are arranged, from N-terminus to C-terminus, in a H-I-J-K orientation, and wherein domain H has a second VL amino acid sequence, domain I has a human CL kappa amino acid sequence, domain J has a human IgG1 CH2 amino acid sequence, and K has a human IgG1 CH3 amino acid sequence with a Y349C, T366S, L368A, and aY407V; (d) the fourth polypeptide chain has a domain L and a domain M, wherein the domains are arranged, from N-terminus to C-terminus, in a L-M orientation, and wherein domain L has a second VH amino acid sequence and domain M has a human IgG1 amino acid sequence; (e) the first and the second polypeptides are associated through an interaction between the A and the F domains and an interaction between the B and the G domains; (f) the third and the fourth polypeptides are associated through an interaction between the H and the L domains and an interaction between the I and the M domains; and (g) the first and the third polypeptides are associated through an interaction between the D and the J domains and an interaction between the E and the K domains to form the binding molecule; (h) domain A and domain F form a first antigen binding site specific for a first antigen; and (i) domain H and domain L form a second antigen binding site specific for a second antigen.

The orthogonal mutations described herein can be further engineered into the B:G paired domains or E:K paired domains.

6.5. EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature.

6.5.1. Example 1—"BC96" Bivalent Antibody Construct

We constructed a new bivalent bispecific construct, termed "BC96", specific for a first antigen, "Antigen A", and a second antigen, "Antigen B", incorporating various orthogonal mutations to drive specific heterodimerization. Salient features of an exemplary "BC96" architecture are illustrated in FIG. 7.

In greater detail, with domain and polypeptide chain references in accordance with FIG. 2, mutations from wild-type sequences indicated in parentheses, and sequences set forth in Section 5 below, the architecture is:

$1^{st}$ polypeptide chain (SEQ ID NO:1)
  Domain A=VI: ("Antigen A")
  Domain B=CH 3 (Y349C; K370R) (SEQ ID NO:5)
  Domain D=CH2 (SEQ) ID NO:6)
  Domain E=CH3 (T366W) (SEQ ID NO:7)
$2^{nd}$ polypeptide chain (SEQ ID NO:2)
  Domain F=VH ("Antigen A")
  Domain G=CH3 (G341A; 53540; E357W) (SEQ ID NO:8)
$3^{rd}$ polypeptide chain (SEQ ID NO:3)
  Domain H=VL ("Antigen B")
  Domain I=CL (Kappa) (SEQ ID N0:9)
  Domain J=CH2 ('SEQ ID NO:10)
  Domain K=CH3 (D356E, L358M, T366S, L368A, Y407V) (SEQ ID NO:11)
$4^{th}$ polypeptide chain (SEQ ID NO:4):
  Domain L=VH ("Antigen B")
  Domain M=CH1 (SEQ ID NO:12).

The A domain and F domain form an antigen binding site (A:F) specific for "Antigen A". The H domain and the L domain associate to form an antigen binding site (H:L) specific for "Antigen B".

The B domain (SEQ ID NO:5) has the sequence of human IgG1 CH3 with two mutations: Y349C and K370R. The Y349C mutation introduces a cysteine that is able to form a disulfide with the cognate C354 mutation in domain G, while the K370R mutation can increase the yield of correctly formed molecules when included in the context of the 357W mutation in chain G.

Domain D (SEQ ID NO:6) has the sequence of human IgG1 CH2

Domain E (SEQ ID NO:7) has the sequence of human IgG1 CH3 with the mutation T366W. The 366W is the "knob" mutation.

Domain G (SEQ ID NO:8) has the sequence of human IgG1 CH3 with the following mutations: G341A, S354C, and E357W. The G341A mutation can increase the yield of correctly formed molecules, the 354C mutation introduces a cysteine that is able to form a disulfide bond with the cognate 349C mutation in Domain B, and the E357W mutation improves the orthogonality of the heterodimeric interface and can increase the yield of correctly formed molecules.

Domain I (SEQ ID NO:9) has the sequence of human C kappa light chain (CIO Domain J (SEQ ID NO:10) has the sequence of human IgG1 CH2 domain, and is identical to the sequence of domain D.

Domain K (SEQ ID NO:11) has the sequence of human IgG1 CH3 with the following changes: D356E, L358M, T366S, L368A, Y407V. The 356E and L358M introduce isoallotype amino acids that reduce immunogenicity. The 366S, 368A, and 407V are "hole" mutations.

Domain M (SEQ ID NO:12) has the sequence of the human IgG1 CH1 region.

Sequences are provided in Section 5, below, with all positions that are mutated from wild type underlined in SEQ ID NOs:1-12. The sequences for the four variable domains are not provided in full, and instead are indicated for antigen binding sites "A" and "B" respectively as <$V_L$-A>, <VH-A>, and <$V_L$-B>, <VH-B>. To indicate the point of junctional fusion, the last three amino acids in a typical human kappa VL domain, "EIK", are included and shown in italics, and the last three amino acids in a typical human VH domain, "VSS", are included and shown in italics.

In contrast to constructs BC-1, BC-6, BC-28, and BC-44, the embodiment of BC-96 depicted in FIG. 7 omits the engineered disulfide in domains E:K. Alternative embodiments that vary from the depicted structure include: (a) including the engineered disulfide bond in domains E:K; (b) flipping the knob-in-hole mutations between domains E:K; (c) flipping the Y+K:S+E pairs in domains B:G; or any subset or combination thereof. In addition, other known orthogonal mutations in CH3 domains can be used, in addition to or instead of the knob-in-hole mutations, in domains E:K.

"BC96" could readily be expressed at high levels using mammalian expression at concentrations greater than 100 µg/ml. We found that the bivalent bispecific "BC96" protein could easily be purified in a single step using a CH1-specific CaptureSelect™ affinity resin from ThermoFisher.

The BC96 protein was expressed along with alternatives to explore the contributions of various mutations to proper assembly of BC96. Results of size exclusion chromatography (SEC) analysis following CH1 purification of each construct demonstrate that presence of the E357W mutation in a first CH3 domain and the K370R mutation in a second CH3 domain that is opposite the first CH3 domain is significant in yielding higher purity of the properly assembled product (FIGS. 8A-8D). BC96 variants lacking both a K370 mutation in Domain B and an E357 mutation in Domain G (FIG. 8A), lacking a K370 mutation in Domain B but containing an E357W mutation in Domain G (FIG. 8B), and containing a K370R mutation in Domain B but lacking an E357 mutation in Domain G (FIG. 8C) were compared to BC96 that contains both a K370R mutation in Domain B and a E357W mutation in Domain G (FIG. 8D). The results demonstrate that presence of an E357W mutation in a first CH3 domain and a K370R mutation in an opposing CH3 domain significantly improves efficiency of dimerization of the two domains and proper assembly of the BC96 antibody construct.

6.5.2. Example 2—Evaluating CH3 Modifications for Improved CH3 Dimerization

In order to evaluate the degree of orthogonality imparted by individual mutations, an asymmetric antibody construct was generated consisting of two sides with distinctly different mass (FIG. 9). Mutations were made in the CH3 domains in the Fc region (Domains E and K) The polypeptides making up each side of the construct were co-expressed and SDS-PAGE and size exclusion chromatography were used to assess assembly of the desired heterodimer product and the homodimer contaminants (FIGS. 10A-10C and 11A-11B).

Each construct evaluated contained a CH3 domain with a Y349C mutation (Domain E) and an opposing CH3 domain with a S354C mutation (Domain K), resulting in an engineered disulfide between the two CH3 domains in the properly assembled product (FIG. 9). Additional substitutions were made in the CH3 sequence of Domain K to generate constructs that also contained an E357W and/or a S364R mutation. Following purification, presence of the large homodimer contaminant (contaminant 1) and the small homodimer contaminant (contaminant 2) could be readily distinguished from the desired heterodimer by size using SDS-PAGE gel.

Results demonstrated significant assembly of both homodimer contaminants in the absence of both E357 and 5364 mutations in the CH3 sequence of Domain K (FIG. 10A). Less contaminant 1 homodimer was generated when the CH3 sequence of Domain K contained an E357W mutation but no 5364 mutation (FIG. 10B and FIG. 11A). In contrast, virtually no contaminant 1 homodimer was detectable when the CH3 sequence of Domain K contained both the E357W and S364R mutations (FIG. 10C and FIG. 11B).

Results in FIGS. 10A-10C show analysis of products by SEC and SDS-PAGE following purification with Protein A. Results in FIGS. 11A-11B show analysis of products by SEC and SDS-PAGE following purification with CH1.

These results suggest that presence of S354C, E357W and S364R mutations in a first CH3 domain and a Y349C mutation in a second CH3 domain opposite the first can significantly improve efficiency of assembly of a product requiring dimerization of the first and second CH3 domains.

7. SEQUENCES

BC96 Chain 1 SEQ ID NO: 1

<VL-A>*EIK*GQPREPQVCTLPPSRDELTKNQVSLTCLVRGFYPSDIAVEWESNGQPE
NNYKTTPPVLDSDGSFFLYSKLTVDKSRWQQGNVFSCSVMHEALHNHYTQKSLSLSP
GKDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPI
EKTISKAKGQPREPQVYTLPPSRDELTKNQVSLWCLVKGFYPSDIAVEWESNGQPEN
NYKTTPPVLDSDGSFFLYSKLTVDKSRWQQGNVFSCSVMHEALHNHYTQKSLSLSPG
K

7. SEQUENCES

BC96 Chain 2 SEQ ID NO: 2

<VH-A>*VSS*AQPREPQVYTLPPCRDWLTKNQVSLTCLVKGFYPSDIAVEWESNGQPE
NNYKTTPPVLDSDGSFFLYSKLTVDKSRWQQGNVFSCSVMHEALHNHYTQKSLSLSP
GK

BC96 Chain 3 SEQ ID NO: 3

<VL-B>*EIK*RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRG
ECDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPI
EKTISKAKGQPREPQVYTLPPSREEMTKNQVSLSCAVKGFYPSDIAVEWESNGQPEN
NYKTTPPVLDSDGSFFLVSKLTVDKSRWQQGNVFSCSVMHEALHNHYTQKSLSLSPG
K

BC96 Chain 4 SEQ ID NO: 4

<VH-B>*VSS*ASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSC

BC96 Domain B SEQ ID NO: 5

GQPREPQVCTLPPSRDELTKNQVSLTCLVRGFYPSDIAVEWESNGQPENNYKTTPPV
LDSDGSFFLYSKLTVDKSRWQQGNVFSCSVMHEALHNHYTQKSLSLSPGK

BC96 Domain D SEQ ID NO: 6

APELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAK

BC96 Domain E SEQ ID NO: 7

GQPREPQVYTLPPSRDELTKNQVSLWCLVKGFYPSDIAVEWESNGQPENNYKTTPPV
LDSDGSFFLYSKLTVDKSRWQQGNVFSCSVMHEALHNHYTQKSLSLSPGK

BC96 Domain G SEQ ID NO: 8

AQPREPQVYTLPPCRDWLTKNQVSLTCLVKGEYPSDIAVEWESNGQPENNYKTTPPV
LDSDGSFFLYSKLTVDKSRWQQGNVFSCSVMHEALHNHYTQKSLSLSPGK

BC96 Domain I SEQ ID NO: 9

RTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

BC96 Domain J SEQ ID NO: 10

APELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAK

BC96 Domain K SEQ ID NO: 11

GQPREPQVYTLPPSREEMTKNQVSLSCAVKGFYPSDIAVEWESNGQPENNYKTTPPV
LDSDGSFFLVSKLTVDKSRWQQGNVFSCSVMHEALHNHYTQKSLSLSPGK

BC96 Domain M SEQ ID NO: 12

ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSC

BC96 Chain 1 DNA sequence (not including VL) SEQ ID NO: 13

GAGATCAAGGGCCAGCCCCGGGAGCCCCAGGTCTGTACCCTGCCGCCGTCACGGGAC
GAACTCACTAAGAACCAAGTGTCCCTGaCTTGCCTGGTCAGAGGATTCTATCCGAGC
GACATCGCCGTGGAGTGGGAGTCCAACGGCCAGCCCGAGAACAACTACAAGACGACA
CCCCCGGTGCTTGACAGCGACGGTTCCTTCTTTTTGTACTCGAAGTTGACCGTCGAT
AAGTCACGCTGGCAACAGGGAAACGTGTTCAGCTGCTCCGTGATGCACGAAGCCCTG
CACAACCACTAGACCCAGAAGTCTCTGAGCCTCTCCCCGGGAAAGGACAAGACTCAC
ACGTGCCCGCCGTGCCCAGCACCTGAGCTGTTGGGAGGTCCTAGCGTGTTCCTGTTC
CCGCCGAAGCCCAAGGACACCCTGATGATTTCGAGGACTCCGAAGTGACCTGTGTG
GTGGTGGATGTGTCCCATGAGGACCCCGAAGTCAAATTCAATTGGTACGTGGATGGA
GTGGAAGTGCACAATGCCAAGACTAAGCCCAGAGAAGAACAGTAGAACTCGACCTAC
CGCGTGGTGTCCGTGCTGACTGTGTTGCATCAGGACTGGCTCAACGGAAAAGAGTAC
AAGTGCAAAGTCTCCAACAAGGCCCTCCCGGCACCGATCGAGAAAACCATCTCGAAA
GCCAAGGGCCAGCCCCGGGAGCCTCAGGTCTACACCCTGCCACCATCGCGGGATGAA
CTCACCAAGAACCAAGTGTCGCTGTGGTGTCTCGTGAAGGGCTTTTACCCTTCCGAC

7. SEQUENCES

```
ATTGCCGTGGAGTGGGAATCCAACGGGCAGCCTGAAAACAACTACAAGACCACCCCG
CCCGTGCTCGACTCGGATGGAAGCTTCTTCCTGTACTCTAAGCTGACCGTGGACAAG
TCCCGGTGGCAGCAGGGAAACGTGTTCAGCTGCTCGGTCATGCACGAAGCCCTGCAT
AACCACTACACCCAGAAGTCACTGTCCCTGAGCCCGGGGAAG
```

BC96 Chain 2 DNA seq (not including VH) SEQ ID NO: 14

```
GTGTCCAGCGCCCAGCCCCGGGAGCCCCAGGTCTACACCCTGCCGCCGTGTCGGGAC
TGGCTCACTAAGAACCAAGTGTCCCTGACTTGCCTGGTCAAGGGATTCTATCCGAGC
GACATCGCCGTGGAGTGGGAGTCCAACGGCCAGCCCGAGAACAACTACAAGACGACA
CCCCCGGTGCTTGACAGCGACGGTTCCTTCTTTTTGTACTCGAAGTTGACCGTCGAT
AAGTCACGCTGGCAACAGGGAAACGTGTTCAGCTGCTCCGTGATGCACGAAGCCCTG
CACAACCACTACACCCAGAAGTCTCTGAGCCTCTCCCCGGGAAAG
```

Chain 3 DNA seq (not including VH) SEQ ID NO: 15

```
GAGATTAAGAGAACCGTCGCAGCCCCCTCCGTGTTCATCTTCCCTCCCTCGGATGAG
CAGCTGAAGTCCGGCACCGCGAGCGTGGTCTGCCTGCTCAACAACTTCTATCCGCGG
GAAGCGAAGGTCCAGTGGAAGGTCGACAACGCCCTGCAGTCGGGAAACTCCCAGGAG
TCCGTGACTGAGCAGGATTCAAAGGACAGCACCTACTCCCTGTCGTCTACCCTCACC
CTGAGCAAGGCCGACTACGAGAAGCACAAGGTCTACGCCTGCGAAGTCACGCACCAA
GGCCTTAGCTCCCCTGTGACCAAGTCATTCAACCGGGGGAGTGCGACAAGACTCAC
ACGTGCCCGCCGTGCCCAGCACCTGAGCTGTTGGGAGGTCCTAGCGTGTTCCTGTTC
CCGCCGAAGCCCAAGGACACCCTGATGATTTCGAGGACTCCGGAAGTGACCTGTGTG
GTGGTGGATGTGTCCCATGAGGACCCCGAAGTCAAATTCAATTGGTACGTGGATGGA
GTGGAAGTGCACAATGCCAAGACTAAGCCCAGAGAAGAACAGTACAACTCGACCTAC
CGCGTGGTGTCCGTGCTGACTGTGTTGCATCAGGACTGGCTCAACGGAAAAGAGTAC
AAGTGCAAAGTCTCCAACAAGGCCCTCCCGGCACCGATCGAGAAAACCATCTCGAAA
GCCAAGGGCCAGCCCCGGGAACCTCAAGTCTACACTCTGCCACCCTCGCGGGAAGAA
ATGACCAAGAACCAAGTGTCCCTGAGCTGTGCCGTGAAGGGCTTCTACCCGTCCGAC
ATCGCCGTGGAATGGGAATCGAACGGGCAGCCGGAGAACAATTACAAGACCACCCCT
CCCGTGCTGGACAGCGATGGATCGTTCTTCCTGGTGTCCAAGCTCACTGTGGACAAG
TCGCGGTGGCAGCAGGGAAACGTGTTTAGCTGCTCCGTGATGCACGAGGCCCTGCAT
AACCACTACACCCAGAAGTCCCTGTCCCTCTCACCCGGGAAG
```

Chain 4 DNA seq (not including VH) SEQ ID NO: 16

```
GTATCAAGCGCCTCAACTAAGGGCCCCTCGGTGTTCCCTCTGGCCCCGAGCTCCAAG
TCGACCTCCGGCGGTACAGCCGCTCTGGGTTGCCTCGTGAAGGACTACTTCCCTGAA
CCAGTGACCGTGTCCTGGAACTCTGGGGCGCTGACCAGCGGGGTGCACACTTTCCCG
GCGGTGCTGCAGTCGTCGGGACTGTACTCCCTGTCCTCCGTCGTGACGGTGCCCTCC
TCCTCACTGGGCACCCAGACTTACATTTGCAACGTGAACCACAAGCCGAGCAACACC
AAGGTCGACAAGAAGGTCGAGCCCAAGTCCTGT
```

BC96-A Chain 1 SEQ ID NO: 17

```
<VL-A>EIKGQPREPQVCTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSP
GKDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPI
EKTISKAKGQPREPQVYTLPPSRDELTKNQVSLWCLVKGFYPSDIAVEWESNGQPEN
NYKTTPPVLDSDGSFFLYSKLTVDKSRWQQGNVFSCSVMHEALHNHYTQKSLSLSPG
K
```

BC96-A Chain 2 SEQ ID NO: 18

```
<VH-A>VSSAQPREPQVYTLPPCRDWLTKNQVRLTCLVKGFYPSDIAVEWESNGQPE
NNYKTTPPVLDSDGSFFLYSKLTVDKSRWQQGNVFSCSVMHEALHNHYTQKSLSLSP
GK
```

BC96-A Domain B SEQ ID NO: 19

```
GQPREPQVCTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK
```

BC96-A Domain G SEQ ID NO: 20

```
AQPREPQVYTLPPCRDWLTKNQVRLTCLVKGFYPSDIAVEWESNGQPENNYKTTPPVLDSDG
SFFLYSKLTVDKSRWQQGNVFSCSVMHEALHNHYTQKSLSLSPGK
```

8. Equivalents and Incorporation by Reference

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. An antibody construct, comprising:

a first polypeptide chain, a second polypeptide chain, a third polypeptide chain, and a fourth polypeptide chain, wherein:

a) the first polypeptide chain comprises a $V_L$ domain, a CH3 domain having the amino acid sequence of SEQ ID NO: 5, a CH2 domain having the amino acid sequence of SEQ ID NO: 6, and a CH3 domain having the amino acid sequence of SEQ ID NO: 7, wherein the domains are ordered, from N terminus to C terminus: $V_L$-CH3-CH2-CH3;

b) the second polypeptide chain comprises a $V_H$ domain and a CH3 domain having the amino acid sequence of SEQ ID NO: 8, wherein the domains are ordered, from N terminus to C terminus: $V_H$-CH3, wherein the $V_L$ domain of the first polypeptide chain and the $V_H$ domain of the second polypeptide chain associate to form a first antigen binding site;

c) the third polypeptide chain comprises a $V_L$ domain, a $C_L$ domain having the amino acid sequence of SEQ ID NO: 9, a CH2 domain having the amino acid sequence of SEQ ID NO: 10, and a CH3 domain having the amino acid sequence of SEQ ID NO: 11, wherein the domains are ordered, from N terminus to C terminus: $V_L$-$C_L$-CH2-CH3; and d) a fourth polypeptide chain comprising a $V_H$ domain and a CH1 domain having the amino acid sequence of SEQ ID NO: 12, wherein the domains are ordered, from N terminus to C terminus: $V_H$-CH1, wherein the $V_L$ domain of the third polypeptide chain and the $V_H$ domain of the fourth polypeptide chain associate to form a second antigen binding site.

* * * * *